United States Patent [19]

Kovats et al.

[11] 3,931,326

[45] Jan. 6, 1976

[54] ALKENOYL-CYCLOHEXADIENES

[75] Inventors: Ervin Kovats, Lausanne; Edouard Demole, Geneva; Gunther Ohloff, Bernex, Geneva, all of Switzerland; Max Stoll, deceased, late of Lully, Geneva, Switzerland, by Suzanne Stoll, executrix

[73] Assignee: Firmenich SA, Geneva, Switzerland

[22] Filed: Nov. 14, 1974

[21] Appl. No.: 523,743

Related U.S. Application Data

[63] Continuation of Ser. No. 35,594, May 7, 1970, abandoned, which is a continuation-in-part of Ser. No. 774,179, Nov. 7, 1968, abandoned.

[30] Foreign Application Priority Data

| Nov. 9, 1967 | Switzerland | 15667/67 |
|---|---|---|
| Nov. 1, 1968 | Switzerland | 16309/68 |
| May 7, 1969 | Switzerland | 6976/69 |
| Aug. 8, 1969 | Switzerland | 12065/69 |
| Apr. 14, 1970 | Switzerland | 5559/70 |
| Apr. 17, 1970 | Switzerland | 5725/70 |

[52] U.S. Cl.......... 260/586 R; 252/522; 260/348 R; 260/348 C; 260/476 R; 260/488 R; 260/514 R; 260/514 K; 260/523 R; 260/544 L; 260/586 C; 260/586 P; 260/586 F; 260/593 R; 260/598; 260/601 R; 260/617 R; 260/617 E; 260/617 F; 260/632 Y; 260/638 R; 260/657; 426/438; 426/553; 426/577; 426/584; 426/590; 426/592; 426/594; 426/597; 426/615; 426/650

[51] Int. Cl.$^2$............................ C07C 49/61
[58] Field of Search................. 260/586 R

[56] References Cited
UNITED STATES PATENTS

| 2,877,271 | 3/1959 | Kaiser | 260/586 R |
|---|---|---|---|
| 3,354,218 | 11/1967 | Aurmatro | 260/586 R |

OTHER PUBLICATIONS

Kovats et al., "Helv. Chim. Acta," Vol. 53, pp. 541–551 (4/4/70).

Bondarev et al., "Chem. Ab.," Vol. 65, p. 16874b, 1966.

*Primary Examiner*—Norman Morgenstern
*Attorney, Agent, or Firm*—Pennie & Edmonds

[57] ABSTRACT

New cycloaliphatic unsaturated ketones and their use as perfuming and odour-modifying agents in the manufacture of perfumes and perfumed products, and as flavouring and taste-modifying agents in the preparation of foodstuffs in general and imitation flavours for foodstuffs, beverages, animal feeds, pharmaceutical preparations and tobacco products.

Methods for the preparation of said cycloaliphatic unsaturated ketones.

10 Claims, No Drawings

ALKENOYL-CYCLOHEXADIENES

This application is a continuation of application Ser. No. 35,594, filed May 7, 1970, which in turn is a continuation-in-part of application Ser. No. 774,179, filed Nov. 7, 1968, both now abandoned.

SUMMARY OF THE INVENTION

The invention relates to a new class of cycloaliphatic unsaturated ketones having the formula

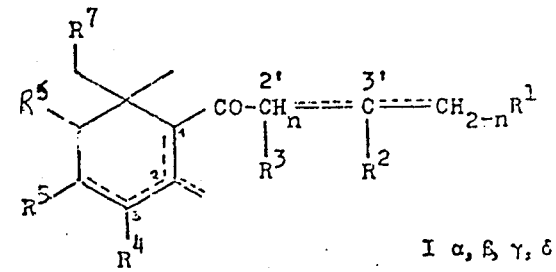

I α, β, γ, δ containing one double bond in position 2'- or 3'- of the acyl side chain and either one double bond in position 1- or 2- (as shown in the above formula, the double bond in the 2 position can be either in the ring or the side chain) or two conjugated double bonds in positions 1- and 2- of the ring, the double bonds being represented by dotted lines, and wherein $n$ is zero or 1, $R^1$, $R^2$ and $R^3$ represent hydrogen or one of them a lower alkyl radical, such as methyl or ethyl, and the others hydrogen and $R^4$, $R^5$, $R^6$ and $R^7$ represent hydrogen or one of them a lower alkyl radical, such as methyl or ethyl, and the others hydrogen.

The invention also relates to methods for the preparation of compounds I, of some of the intermediates used in their preparation and some of their derivatives and to the use of said compounds as perfuming and odourmodifying agents in the manufacture of perfumes and perfumed products, and as flavouring and taste-modifying agents in the manufacture of artificial flavours for foodstuffs, beverages, animal feeds, pharmaceuticals and tobacco.

DESCRIPTION OF THE PREFERRED EMBODIMENTS

The compounds of the invention have particularly interesting and valuable organoleptic properties and, consequently, they are useful as fragrances in the perfume industry, as ingredients for the preparation of artificial flavours and as flavour additives in foodstuffs, animal feeds, beverages, pharmaceutical preparations and tobacco products.

The term "foodstuff" is used in this specification in its broadest sense and is meant to include also products such as coffee, tea and cocoa. In particular, the new ketones and some of their intermediates can be used as odoriferous ingredients in concentrated or diluted perfumes and in perfumed products such as soaps, detergents, cosmetic products, waxes and any other products which may be perfumed to make them commercially more attractive.

Furthermore, the new compounds are very useful as ingredients in the preparation of artificial essential oils such as jasmin oil, geranium Bourbon oil, rose oil and others.

The compounds of the invention increase the power and the diffusion ability of perfume compositions and impart to them a natural richness.

The compounds of the invention possess also very interesting flavouring properties. Depending on the nature of the products to which they are added, they will develop fruity, herb-like, winy, woody, floral or waxy flavour notes or any combinations of these flavour notes. In some instances they will impart to products a red berrylike flavour and can be used for improving the taste and aroma of artificial strawberry, cranberry, cherry or redcurrant flavour compositions and the like. Surprisingly, the new ketones can even be used for enhancing the taste and flavour of such products as honey and red wines.

The proportions in which the new compounds can be used to produce desirable odoriferous effects vary within wide limits. In the preparation of perfume compositions, for instance, interesting effects can be obtained with proportions as low as about 100 ppm to about 5 % of the total weight of a perfume composition. Depending on the odoriferous effects wanted, the proportions of the ketones can be increased to about 10 % or even more.

When the new ketones are used as flavouring agents or additives for modifying the organoleptic properties of foodstuffs, animal feeds, beverages, pharmaceutical preparations and tobacco products, the new compounds can be used in proportions which, again, vary within wide limits.

Interesting flavouring effects, for instance, can be achieved by using the compounds of the invention in proportions from 0.1 to 10 ppm based on the weight of the products to be flavoured. However, these proportions can be increased beyond 10 ppm up to about 100 ppm in order to achieve special flavouring effects. In the preparation of flavouring compositions by admixing the new compounds to other aromatics, the said compounds can be used, for example, in proportions of about 0.1 % to about 15 % of the total weight of the flavouring composition. In many cases average proportions of about 1 to 10 % by weight will give the desired results.

It is to be understood that the proportions given above are in no way absolute values and that higher or lower concentrations of the new compounds may be used depending on the specific odoriferous or flavouring effects to be developed.

According to the invention, the methods of preparation of the compounds of formula I are either of general nature or of more specific type.

According to the invention, a general method for the preparation of compounds of formula

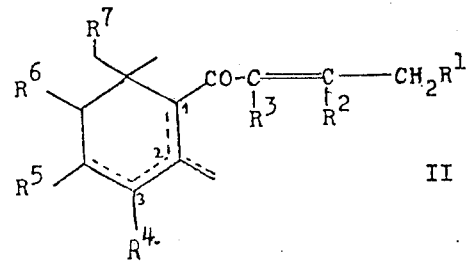

II containing either one double bond in position 1- or 2- or two conjugated double bonds in positions 1- and 3- of the ring, the double bonds being represented by dotted lines, and wherein $R^1$, $R^2$ and $R^3$ represent hydrogen or one of them a lower alkyl radical, such as methyl or ethyl, and the others hydrogen, and $R^4$, $R^5$, $R^6$ and $R^7$ represent hydrogen or one of them a lower alkyl radical, for example methyl or ethyl, and the others hydrogen, comprises acylating organo-metallic propene derivatives having the formula

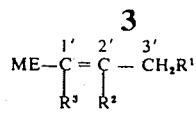

III wherein the symbols $R^1$, $R^2$ and $R^3$ have the same meaning as above and ME represents a metallic function such as Li, Zn, Cd and Mg-halogen, with cyclogeranoyl or safranyl derivatives having the formula

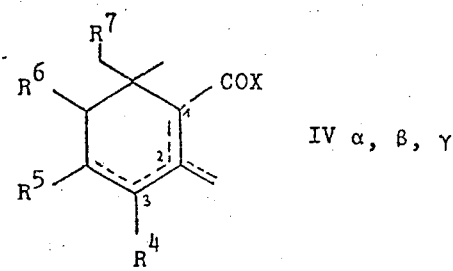

IV α, β, γ cyclogeranoyl derivatives, geranoyl halogenides such as, for instance, chlorides, bromides or iodides or geraniate derivatives such as methyl, ethyl or lithium geraniate. The cyclogeranoyl and safranyl derivatives used in the above mentioned process can be synthesized according to different methods, some of which are described hereinafter. For instance, 1. The cyclogeranoyl derivatives of structure α- and β- can be synthesized from the corresponding cyclogeranic acids by usual methods. The cyclogeranic acids may be obtained from the corresponding citral derivatives according to known methods [cf.: Gildemeister & Hoffmann, Die Aetherischen Oele, III d, pp. 137–138, Akademie-Verlag, Berlin (1966)]. The process for the preparation of the cyclogeranoyl derivatives of structure α- and β- can be illustrated by the following scheme A wherein the dotted lines and the symbols R have the same meaning as above.

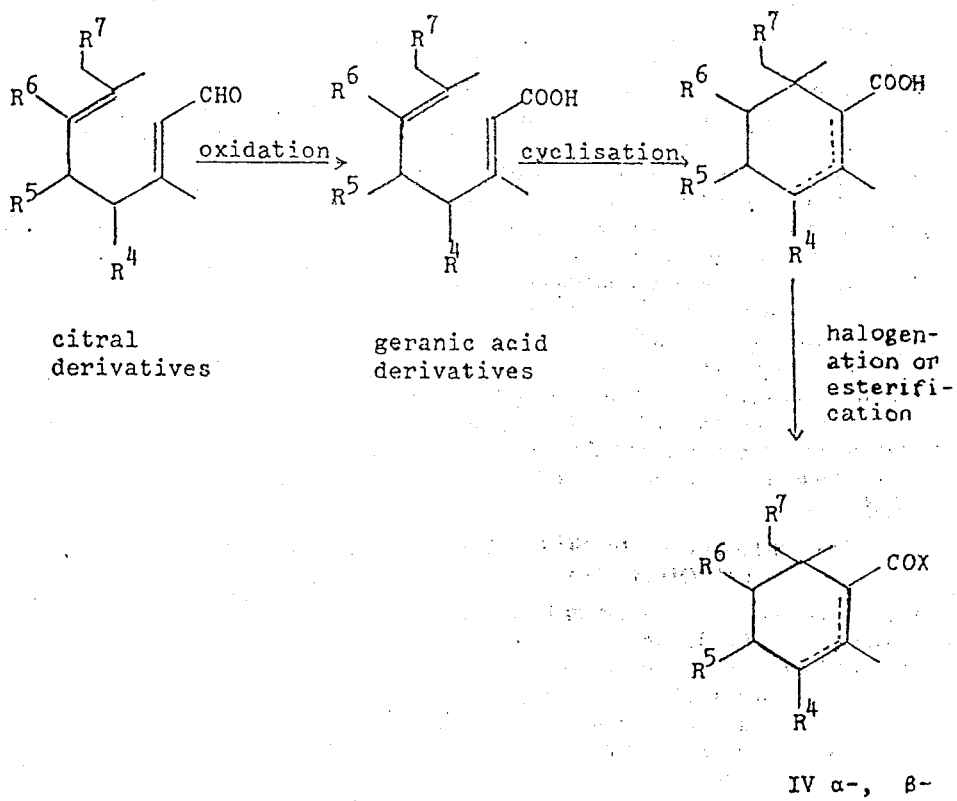

{ α = endocyclic double bond in position 2-
{ β = endocyclic double bond in position 1-
{ γ = exocyclic double bond in position 2- wherein the dotted lines and the symbols $R^4$, $R^5$, $R^6$ and $R^7$ have the same meaning as above and wherein the symbol X represents a leaving group such as halogen, O-alkyl, O-aryl, O-CO-aryl, O-CO-alkyl.

A preferred mode of operation consists in using, as

2. The cyclogeranoyl derivatives of structure α-, β- can also be obtained by cyclisation of the corresponding citral derivatives [e.g. cf.: Bedoukian, Perfumery and Flavoring Synthetics, Elsevier, New York (1967)], whereas the cyclogeranoyl derivatives of structure γ- are obtained by isomerization of β-cyclocitrals. The aldehydic group of cyclocitrals is oxidised to —COOH and finally this latter is transformed into —COX by the usual means. Scheme B illustrates this process. The dotted lines and the symbols R have the same meaning as above.

Scheme B:

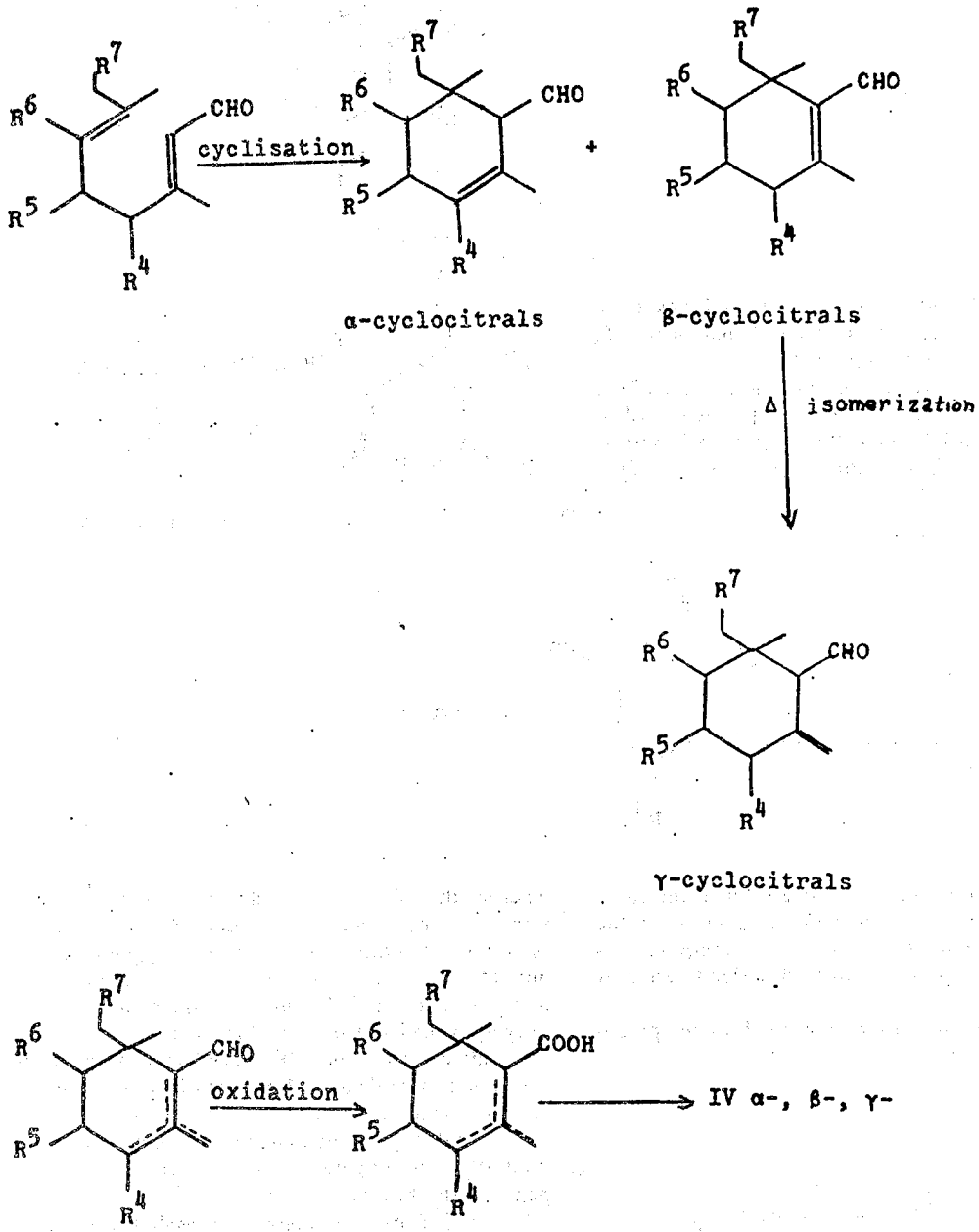

α-cyclocitrals

β-cyclocitrals

γ-cyclocitrals

3. The cyclogeranoyl derivatives of structure γ-, where X = O-alkyl, can be prepared according to Helv. Chim. Acta 41, 1359 (1958) from an α-alkoxycarbonyl derivative of cyclohexanone. By condensation of these derivatives with an ethyl haloacetate in the presence of zinc a diester is obtained which, after dehydration, partial saponification and monodecarboxylation, gives the desired γ-compounds. This process is illustrated in Scheme C hereinafter. The dotted lines and the symbols R have the same meaning as above.

Scheme C:

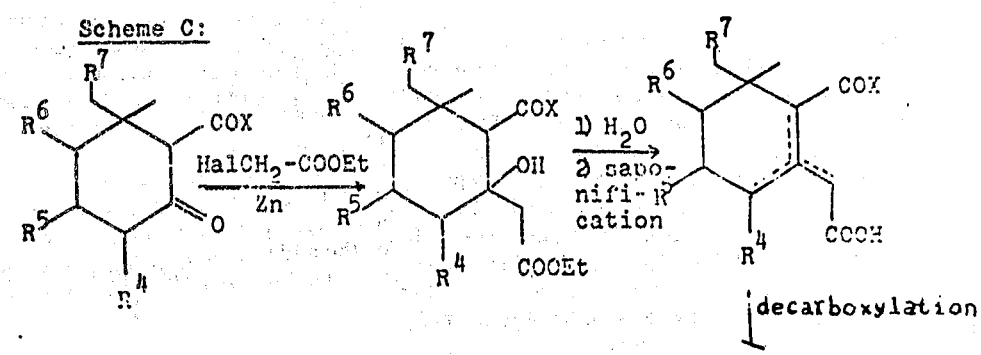

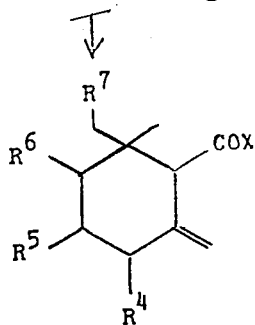

IV γ-

The α-alkoxycarbonyl derivatives of cyclohexanone may be obtained according to Helv. Chim. Acta 35, 1753 (1952) from methylheptenone.

4. The safranyl derivatives used in the process of the present invention can be obtained simply by dehydrogenating the corresponding β-cyclogeranoyl derivatives as follows. The substituents R have the same meaning as above.

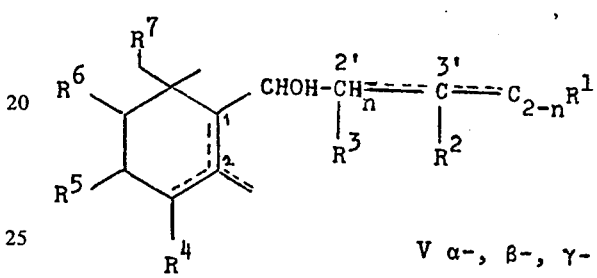

V α-, β-, γ-

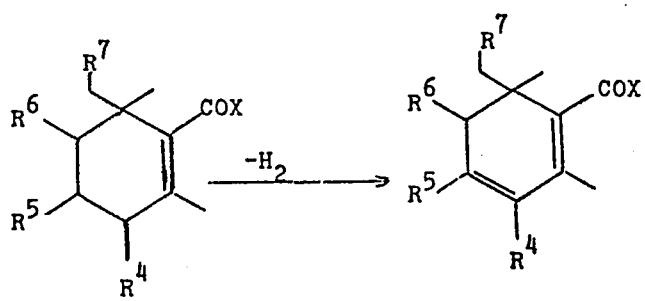

IV δ

The dehydrogenation may be carried out in the same way as that described for one of the process of the invention which consists in converting compound Iα and Iβ into Iδ. This process will be described hereafter ( see p. 23 ).

According to the invention, a method for the preparation of ketones of formula

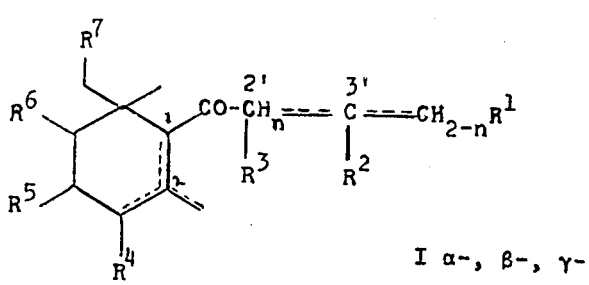

I α-, β-, γ- containing one double bond in position 2'- or 3'- of the acyl side-chain and one double bond in position 1- (structure β-) or 2- (structure α-, endocyclic double bond; structure γ-, exocyclic double bond) of the cycle, the double bonds being represented by dotted lines, and wherein $n$ is zero or 1, $R^1$, $R^2$ and $R^3$ represent hydrogen or one of them a lower alkyl radical such as methyl or ethyl, and the others hydrogen, and $R^4$, $R^5$, $R^6$ and $R^7$ represent hydrogen or one of them a lower alkyl radical, such as methyl or ethyl, and the others hydrogen, comprises oxidising an alcohol of formula wherein the dotted lines and the symbols R have the same meaning as those of formula I. Silver carbonate in presence of diatomaceous earth, oxygen-containing derivatives of a transition element such as chromium, manganese or nickel, pure or atmospheric gaseous oxygen in presence of activators, such as, for example free radicals initiators, can be used as oxidising agents. Chromium trioxide and manganese dioxide are preferably used [see for example, J. Org. Chem. 26, 4814 (1961)]. $MnO_2$ is a cheap oxidising agent which can be used at room temperature in an inert solvent such as pentane and hexane.

When it is used to convert V to I, the geometric isomerism of the material being oxidised (cis- or trans-alcohols V or mixture thereof) remains practically unchanged. When $CrO_3$ is used, preferably in the presence of an organic base such as pyridine, the ketone resulting from either the cis- or the trans-alcohols V has the geometry trans-. The starting compounds V which possess interesting organoleptic properties and, consequently, can be advantageously used in the perfume industry, can be prepared according to usual methods by the addition to α-, β- or γ-cyclocitrals of an organometallic derivative having the formula

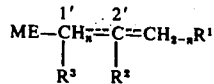

III b containing one double bond in position 1'- or 2'-, the double bond being represented by the dotted lines, and wherein ME represents a metallic function such as, for instance, Li or BrMg, $R^1$, $R^2$ and $R^3$ have the same meaning as above and n is zero or 1, and subsequent hydrolysis of the addition product.

derivatives. In these schemes the symbols R have the same meaning as indicated above, ME represents a metallic function and a indicates an addition reaction of an organo-metallic reactant on a ketone [see for example, D. J. Cram and G. S. Hammond, Organic Chemistry, McGraw-Hill, New York (1959) p. 294]

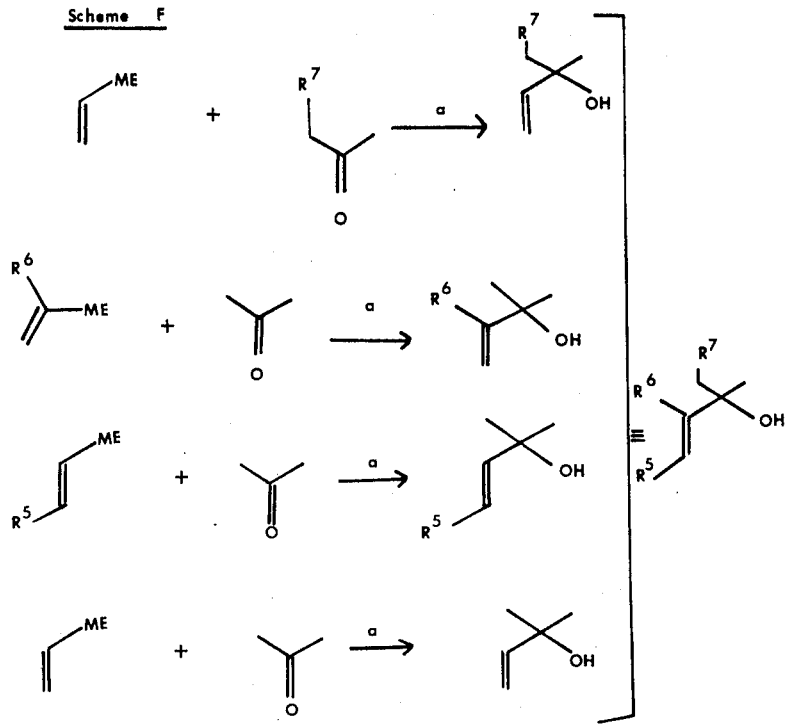

Scheme F

The above process is illustrated by scheme E herebelow, wherein the dotted lines and the symbols R have the same meaning as above.

Scheme C:

b: Carrol reaction [see for example J. Chem. Soc. pp. 704, 1266 (1940); p. 507 (1941)]

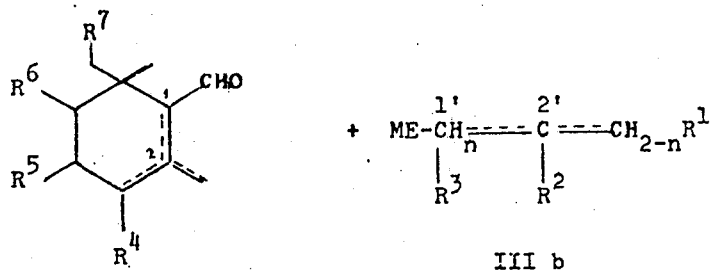

Scheme E

α-, β-, γ-cyclicitrals

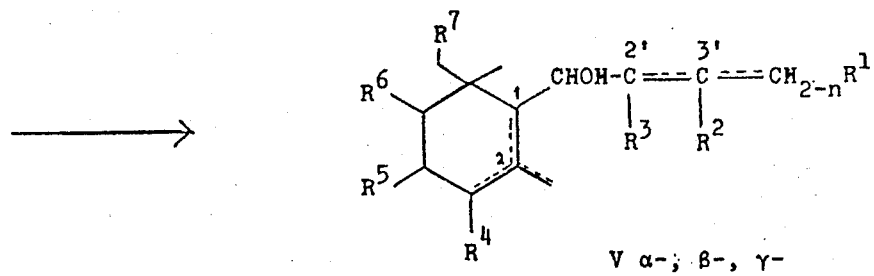

V α-; β-, γ-

The α-, β- and γ-cyclocitrals can be prepared from citral derivatives as indicated in scheme B (see above) and schemes F and G will illustrate a few examples of reactions for the preparation of such starting citral c: Reactions for the conversion of methylheptenones to the corresponding citrals [see for example Bedoukian, Perfumery and Flavoring Synthetics, Elsevier, New York (1967), p. 102–103]

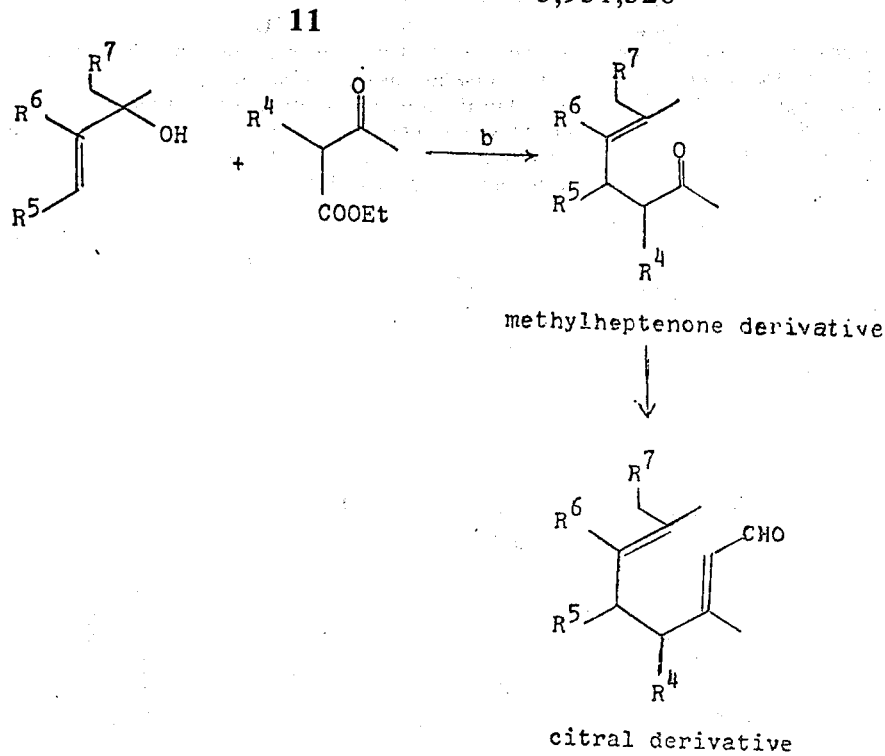

methylheptenone derivative citral derivative

The alcohol of formula

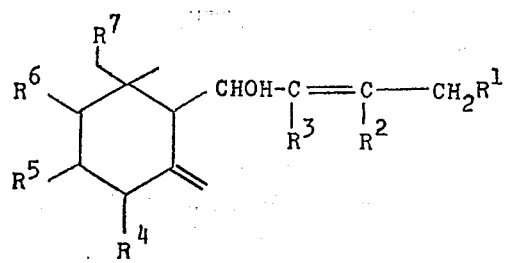

V γ-a wherein the symbol $R^2$ represents hydrogen, $R^1$ and $R^3$ represent hydrogen or one of them a lower alkyl radical, such as methyl or ethyl, and the other hydrogen, and $R^4$, $R^5$, $R^6$ and $R^7$ have the same meaning as above, can be prepared by isomerisation and simultaneous reduction of an epoxide having the formula

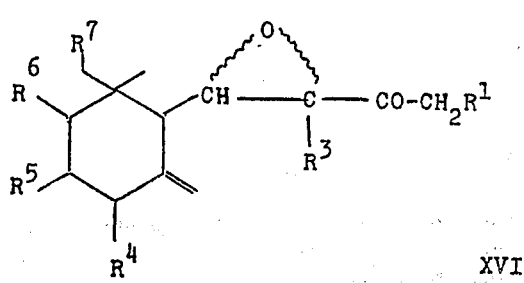

XVI wherein the R's have the same meaning as above [see Tetrahedron 19, 1091 (1963) and J. Org. Chem. 26, 3615 (1961)].

According to the invention, the ketones of formula I α- and I β-, wherein the double bond of the acyl side-chain is in position 2'-, are prepared by cyclising, by means of an acidic cyclising agent, a "pseudo"-ketone of formula

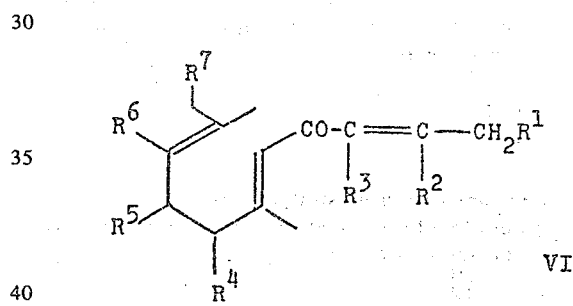

VI wherein the R's ahave the same meaning as in formula I. The cyclisation can be carried out under the same conditions used for cyclising the 1,5-dieno compounds, for example for cyclising citral to cyclocitral or geranic acid to cyclogeranic acid [see for example, P. Z. Bedoukian, Perfumery and Flavoring Synthetics, Elseyier, New York (1967)].

When cyclising agents such as proton acids are used to effect the cyclisation the resulting ketone I possesses generally the structure -β, that is to say with the double bond in the ring conjugated with the CO-group (position 1- of the ring). When cyclising agents such as Lewis acids are used in the cyclisation, for instance boron trifluoroetherate or $SnCl_4$, the resulting ketone I possesses generally the structure α-, that is to say with the double bond in position 2- of the ring. The cyclisation is preferably carried out by means of $SnCl_4$ in an inert solvent such as benzene or toluene.

In the above mentioned process, the starting "pseudo"-ketones, which are new odoriferous compounds and can be advantageously used in the perfume industry, can be easily obtained by reacting a citral derivative (see scheme G) with an organo-metallic derivative of propene (see formula III above), under conditions analogous to those described for the preparation of alcohols V, and subsequent oxidation of the resulting alcohol with am oxidising agent. Said oxidation can be carried out by means of the same oxidising agents and under reaction conditions analogous to those used for the oxidation of the alcohols having formula V.
The pseudo-ketones VI can also be prepared from methylheptenone derivatives (cf. scheme G) according to the process shown in scheme H hereinbelow wherein the symbols R have the same meaning as above.
Scheme H:
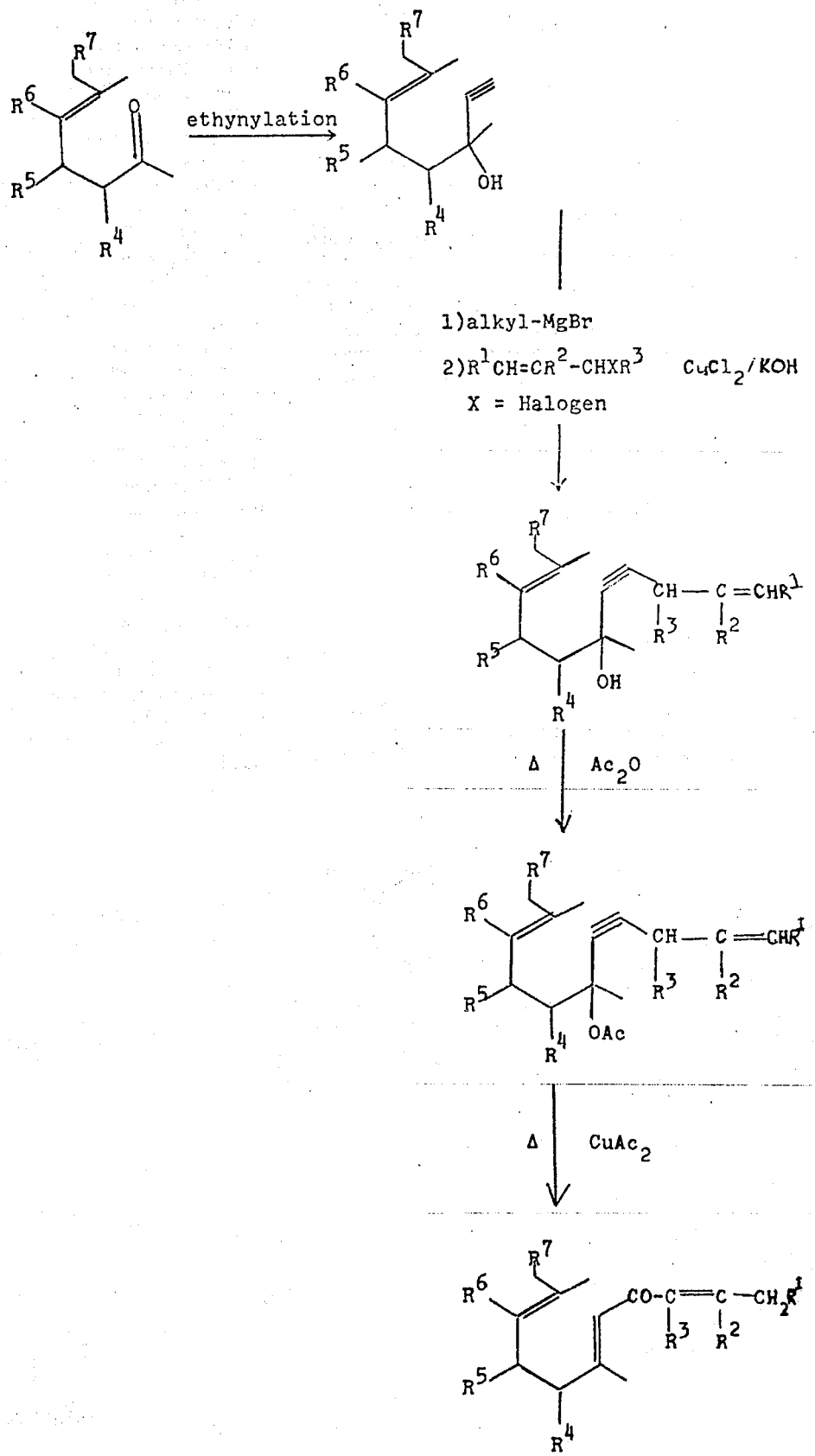
VI According to the invention a method for the preparation of compounds having the formula

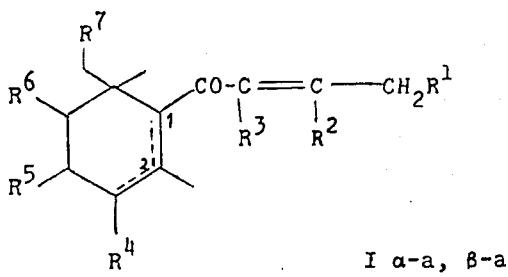

I α-a, β-a containing one double bond in position 1- or 2- of the cycle, the double bonds being represented by dotted lines, wherein $R^1$, $R^2$, and $R^3$ represent hydrogen or $R^1$ a lower alkyl radical, such as methyl or ethyl, and the others hydrogen, and $R^4$, $R^5$, $R^6$ and $R^7$ represent hydrogen or one of them a lower alkyl radical, such as methyl or ethyl, and the others hydrogen, comprises partially hydrogenating the triple bond of an acetylenic ketone having the formula

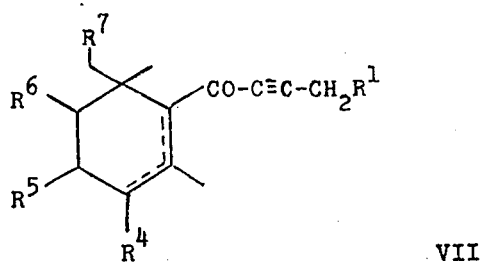

VII wherein the dotted lines and the symbols R have the same meaning as in formula I. The partial hydrogenation can be performed in the presence of a Lindlar type catalyst (deactivated Pd/C catalyst, see Helv. Chim. Acta 35, 446 (1952) according to usual methods. The ketones I α-a and I β-a resulting from the above partial hydrogenation have the configuration cis-. The corresponding transisomers are prepared according to the invention by isomerisation with an acid in an inert solvent. Acids which can be used for carrying out the above isomerisation comprise proton acids, such as those ordinarily used to produce enolisation of ketones, for instance p-toluenesulfonic acid, hydrochloric acid and trifluoracetic acid. Lewis acids, such as for instance boron trifluoride or iodine, can also be used. The isomerisation is best carried out in an inert solvent such as an aromatic hydrocarbon, for example benzene or toluene, an aliphatic or cycloaliphatic hydrocarbon, e.g. heptane or cyclohexane, or an ether, e.g. monoglyme, diglyme or dioxan. The temperature at which the isomerisation can be carried out is not critical. For instance, the isomerisation can be carried out by mixing the substance to be isomerised together with the solvent and a catalytic amount of the acidic isomerising agent and allowing the mixture to stand at room temperature for several hours, e.g. 12 hours. At lower temperature the reaction time may increase considerably. At temperatures higher than the room temperature the reaction time may be shortened. However, above 100° C unwanted side reactions may occur and it is preferable to carry out the isomerisation below 100° C.

The acetylenic ketones VII which are used as starting materials in the above process are themselves odoriferous new compounds which can be used in the perfume industry. They possess valuable floral fragrances. They can be prepared by a method which comprises reacting α- or β-cyclocitrals with organo-metallic derivatives of propyne, subsequently hydrolysing the reaction products to acetylenic alcohols and oxidising the latter to the ketones VII.

This method can be illustrated by scheme I underneath.

Scheme I

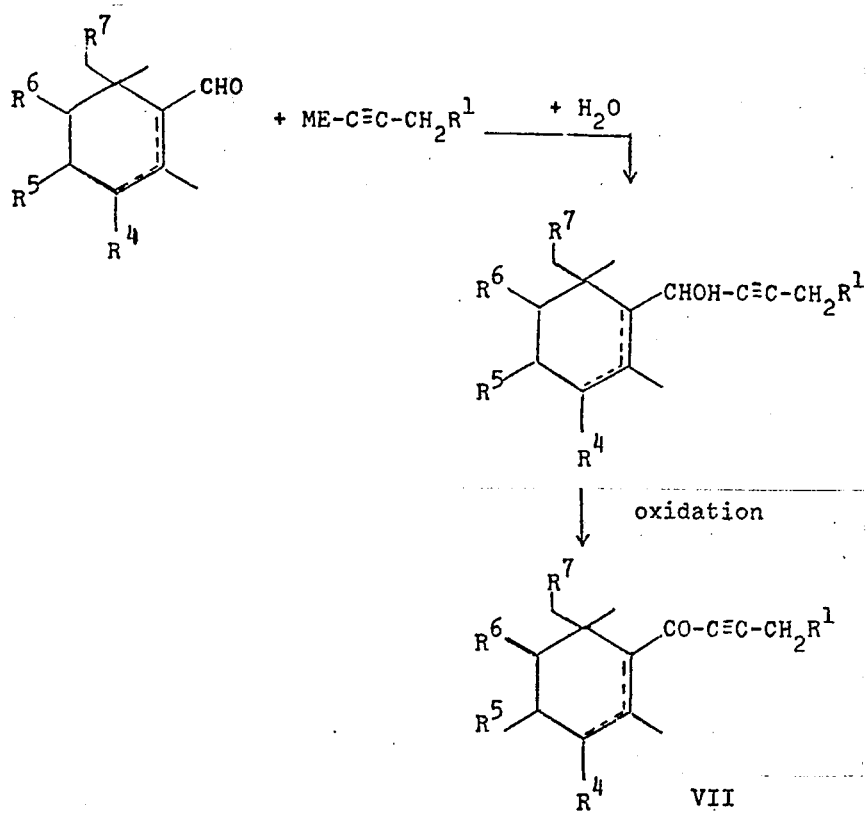

In scheme I the dotted lines and the symbols R have the same meaning as above. The symbol ME represents a metal function such as those commonly found in organo-metallic compounds, for instance alkali metals, mercury, zinc, cadmium and magnesium. In cases where ME represents a divalent metal, i.e. for instance Mg, the second valence bond can be linked to a negative substituent such as for instance Br, Cl or I. For the oxidation of the acetylenic alcohols to ketones VII, the same oxidising agents used for the oxidation of alcohols V to ketones I can be used under similar conditions. Good results are obtained by carrying out the oxidation with $MnO_2$ in a cheap inert solvent such as hexane, cyclohexane or petroleum ether.

The acetylenic ketones of formula VII can also be prepared by the direct acylation, according to usual procedures, of organo-metallic propyne derivatives of formula

wherein ME represents a metallic function such as for instance Li, Na or K with cyclogeranoyl derivatives having the formula IV α- or IV β- (see scheme A above).

According to the invention, a method for the preparation of compounds having the formula

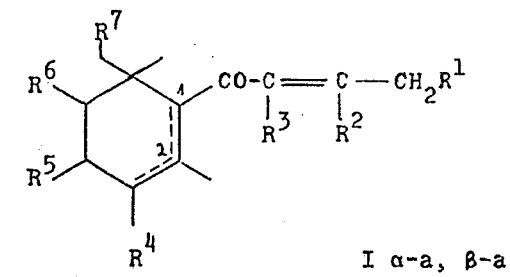

containing one double bond in position 1- or 2- of the ring, the double bond being represented by dotted lines, wherein $R^1$, $R^2$ and $R^3$ represent hydrogen or one of them a lower alkyl radical, such as methyl or ethyl, and the others hydrogen, and $R^4$, $R^5$, $R^6$ and $R^7$ represent hydrogen or one of them a lower alkyl radical, such as methyl or ethyl, and the others hydrogen, comprises isomerising compounds having the formula

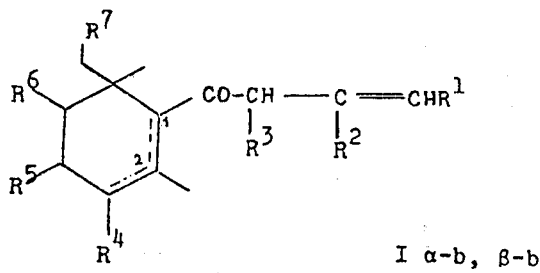

wherein the dotted lines and the symbols R have the same meaning as above, by means of an acidic or basic isomerising agent or by means of heat. As acidic isomerising agent a strong mineral or organic acid, such as for instance sulphuric acid, phosphoric acid, gaseous hydrochloric acid, perchloric acid, p-toluenesulfonic acid and trifluoracetic acid can be used. p-Toluensulfonic acid is preferably used. The isomerisation by means of an acidic isomerising agent can be carried out in an organic solvent. For instance, most of the commonly used organic solvents such as aliphatic cycloaliphatic hydrocarbons, aromatic hydrocarbons, chlorinated hydrocarbons or esters and ethers can be conveniently used. Benzene is preferably used.

As basic isomerising agent an alkali, an alkali-buffer or an organic base can be used.

According to the invention a method for the preparation of compounds having the formula

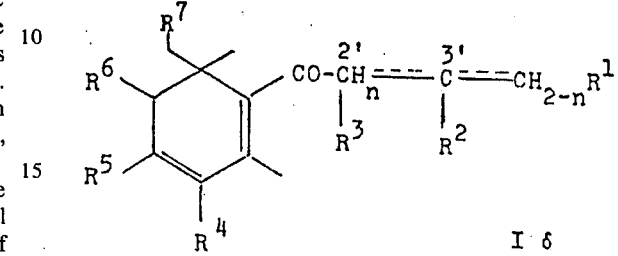

containing one double bond in position 2'- or 3'- of the acyl side-chain, the double bond being represented by dotted lines, wherein n is zero or 1, $R^1$, $R^2$ and $R^3$ represent hydrogen or one of them a lower alkyl radical, such as methyl or ethyl, and the others hydrogen, and $R^4$, $R^5$, $R^6$ and $R^7$ represent hydrogen or one of them a lower alkyl radical, such as methyl or ethyl, and the others hydrogen, comprises dehydrogenating the compounds of formula

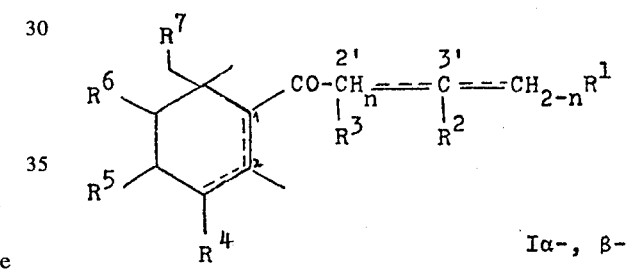

wherein the dotted lines and the symbols R have the same meaning as above.

The dehydrogenation can be carried out by halogenating the cyclohexenic ring in the allylic position and subsequently dehydrohalogenating the product of halogenation. As halogenating agents, commonly known halogenating reactants of the allylic position such as for instance, haloamides, for example N-bromosuccinimide, N-bromoacetamide, N-dimethyldibromohydantoin and their chlorinated analogues can be used.

According to the usual procedure, N-bromosuccinimide is preferably used [see Chem. Rev. 63, 21 (1963)].

The halogenation in the allylic position can be carried out in an inert solvent at a mild temperature. For instance, a chlorinated solvent such as $CCl_4$, $CHCl_3$, $CH_2Cl_2$, dichloroethane, tetrachloroethane and trichloroethylene or a mixture of said solvents and temperature between about 20° and 100° can be considered as convenient. It is possible to operate at higher temperatures, but the course of the reaction becomes difficult to follow. Preferably, the allylic halogenation is carried out in a mixture of $CCl_4$ and $CH_2Cl_2$ or $CHCl_3$ at a temperature comprised between 40° and 70° C.

The presence in the reaction mixture of an initiator such as α-α'-azo-bis-isobutyronitrile or benzoyl peroxide or the use of actinic radiations is advantageous. In such case in fact, the initial reaction temperature can be appreciably lower than in the absence of such an initiator; an easier control of the course of the reaction is thus possible.

The dehydrohalogenation of the resulting halogenated product of the above reaction can be carried out without isolation and/or previous purification of said halogenated product and can be promoted by organic bases such as for instance tertiary amines. As tertiary amines piperidine, morpholine, tributylamine, diethylaniline and dimethylaniline can be used. Preferably, diethylaniline is used owing to its low volatility but other tertiary amines can be equally effective.

The temperature of the dehydrohalogenation is comprised between 100° and 150° C. However, it is possible to operate at temperatures below or above these limits but at temperatures below 100° C the reaction time may become longer, whereas at temperatures above 150° C the product may undergo a partial decomposition.

According to the invention a method for the preparation of compounds having the formula

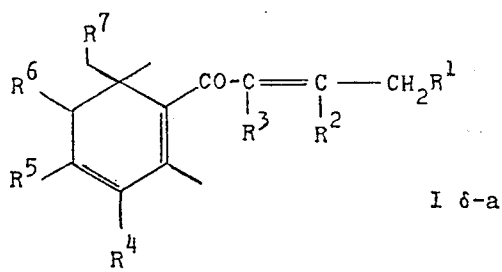

I δ-a wherein $R^1$, $R^2$ and $R^3$ represent hydrogen or one of them a lower alkyl radical, such as methyl or ethyl, and the others hydrogen and $R^4$, $R^5$, $R^6$ and $R^7$ represent hydrogen or one of them a lower alkyl radical, such as methyl or ethyl, and the others hydrogen, comprises treating with an acidic agent an epoxy-compound of formula

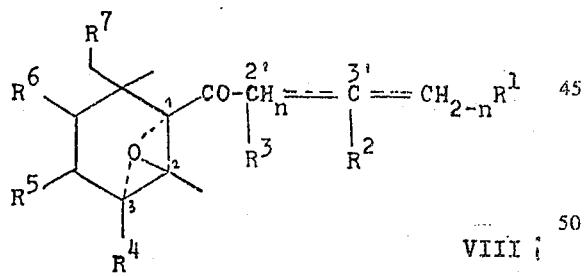

VIII containing one double bond in position 2'-or 3'-of the acyl side-chain, the double bond being represented by dotted lines, wherein n is zero or 1, and wherein the oxygen atom of the epoxide cycle is bound to the positions 1- and 2- or 2- and 3- of the cycle and the symbols R have the same meaning as above.

As acidic agents, mineral or organic acids such as, for instance, hydrochloric acid, phosphoric acid, sulphuric acid, p-toluensulfonic acid and trifluoracetic acid or acidic diatomaceous earth can be used. The reaction can be carried out in an organic solvent such as for example benzene, toluene, tetrahydrofuran, dioxan or ethyl acetate at a temperature comprised between about 20° and about 100° C. Preferably, phosphoric acid in dioxan or tetrahydrofuran is used and the reaction is carried out at the boiling temperature of said solvents.

The above reaction proceeds through the formation of an hydroxy intermediate of formula

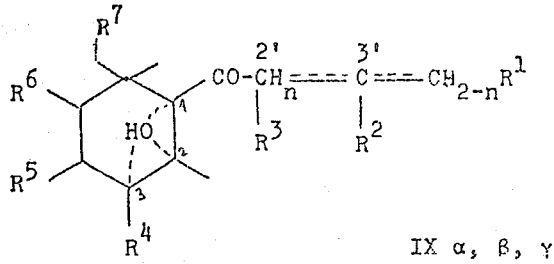

IX α, β, γ containing one double bond in position 2'- or 3'- of the acyl side-chain wherein the symbols R have the same meaning as above, and wherein the OH- radical is bound to position 1-, 2- or 3- of the cycle. Compounds IX, such as 2,6,6-trimethyl-1-hydroxy-1-crotoncyl-2cyclohexene, are new and possess very interesting organoleptic properties and are useful in the flavour and perfume industry.

According to another method of the invention, compounds of formula Iδ-a are prepared by oxidising, by means of one or more than one oxidising agent, a compound of formula

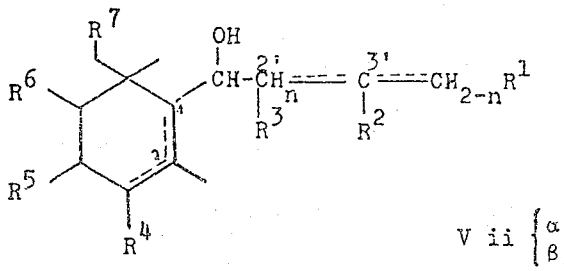

Vii { α β containing one double bond in position 2'- or 3'- of the acyl side-chain and one double bond in position 1- or 2- of the cycle, the double bonds being represented by dotted lines, wherein n is zero or 1 and wherein the symbols R have the same meaning as in formula Iδ-a.

As oxidising agent, an oxygen containing derivative of an alkali metals, such as potassium chromate or bichromate, or of a transition element, such as chrome, manganese or nickel, can be used. The oxidation is preferably carried out by $CrO_3$ in a mineral or organic acid.

The oxidation of compounds Vii to ketones Iδ-a can also be carried out by the successive use of at least two different oxidising agents such as, for instance, a peracid and $CrO_3$. According to a preferred mode of operation, a peracid in a buffered hydrophobic solvent and an acid aqueous solution of $CrO_3$ are added successively to the alcohol Vii at room temperature. In this process a peracid such peracetic acid, performic acid, perbenzoic acid, perphthalic acid or m-chloroperbenzoic acid in a solvent such as, for instance, chloroform, methylene chloride, benzene or trichloroethylene in the presence of a buffer such as an alkali acetate, can be used. Preferably, $CrO_3$ is then used in an aqueous solution acidified with $H_2SO_4$.

The above method can be summarised by scheme J hereinafter.

Scheme J

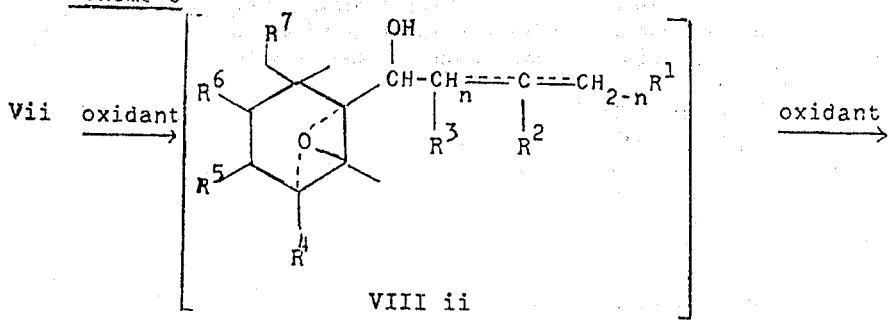

VIII ii

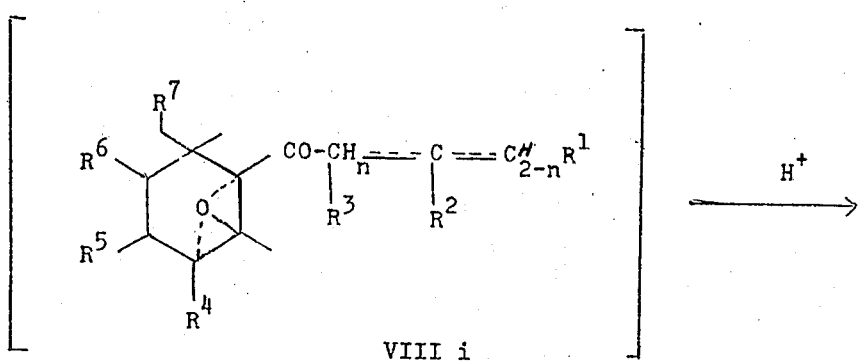

VIII i

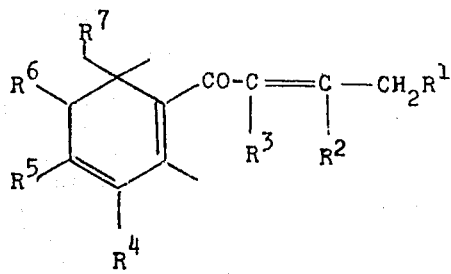

I δ-a

In the above scheme J the dotted lines, the index *n* and the symbols R have the same meaning as in formula VIIIi (see above).

According to the above described process, the epoxy intermediates are not isolated; however, when required these epoxides, which are new odoriferous products and can be advantageously used in the perfume and flavour industry, are prepared according to the invention by epoxidising a compound of formula

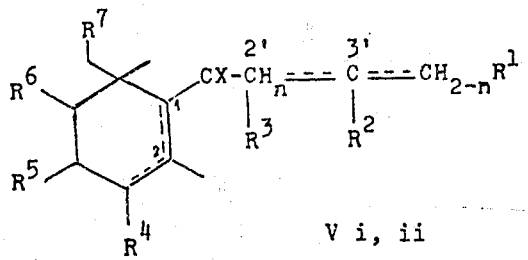

V i, ii
i) X = O
ii) X = {-H, -OH} wherein the dotted lines, the index n and the symbols R have the same meaning as above and X represents an oxygen or hydrogen and an —OH group. As epoxidising agents the same peracids described above for the oxidation of V ii can be used. The reaction can be carried out in an analogous way.

The epoxy-ketones VIII i are obtained according to the invention by oxidation of compound VIII ii.

As oxidising agents, the reactants commonly known to oxidise a secondary hydroxylic function to a ketonic function such as oxygen-containing derivatives of silver or of a transition element such as chrome manganese or nickel, can be conveniently used.

An alkali bichromate in acidic solution is preferably used.

The compounds of general formula I possess in their side-chain a cis- or trans- configuration. Some of the methods of the invention give generally mixtures in which the respective amounts of the two isomers vary within broad limits. As a general rule, for economic reasons the mixtures obtained by one of the above process are used in the perfume industry without further purification or separation. However, if necessary the two isomeric forms can be separated by the usual methods, for instance, by column or vapour phase chromatography. Moreover, cis-isomers isomerise to the corresponding trans-isomers in the presence of acids. By actinic radiations an equilibrium is established between the two forms, in other words, by irradiating one or the other of the two isomers, a mixture, in which the amount ratio of the two isomers is constant, will be formed. Such ratio will not change even if the radiation time is protracted.

It has been found that bicyclic compounds of formula

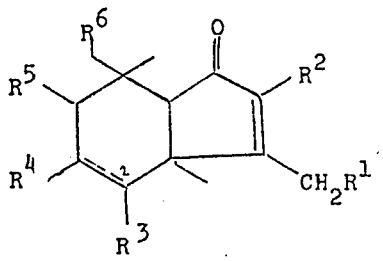

X i containing either a six-membered saturated carbon cycle or an hexenic ring wherein the double bond is in position 2-, the double bond being represented by the dotted line, and wherein the symbols $R^1$ and $R^2$ represent hydrogen or one of them a lower alkyl radical, such as methyl or ethyl, and the other hydrogen, and $R^3$, $R^4$, $R^5$ and $R^6$ represent hydrogen or one of them a lower alkyl radical, such as methyl or ethyl, and the others hydrogen, and of formula

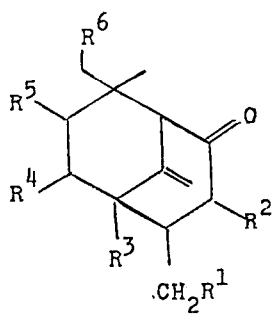

XII and

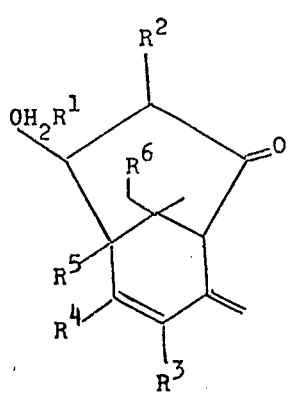

XIV wherein the symbols R have the same meaning as above, possess very valuable organoleptic properties and can be conveniently used in the perfume and flavour industry.

According to a method of the invention, compounds Xi are obtained by cyclising by means of an acidic or basic agents a compound of formula

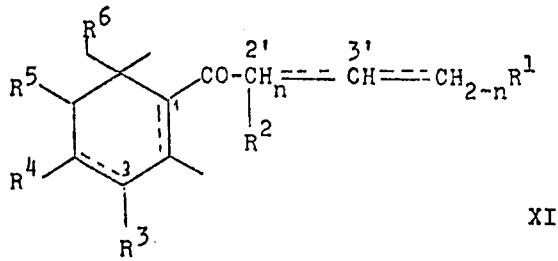

XI containing one double bond in position 2'- or 3'- of the acyl side-chain and containing either one double bond in position 1- or two conjugated double bonds in positions 1- and 3- of the ring, the double bonds being represented by the dotted lines, and wherein the index $n$ is zero or 1 and the symbols R have the same meaning as in formula Xi.

The cyclisation can be carried out by using as acidic agent either a mineral or organic protonic acid, such as hydrochloric acid, phosphoric acid, sulphuric acid, acidic diatomaceous earth, p-toluenesulfonic acid or trifluoracetic acid, or Lewis acids, such as $BF_3$, $AlCl_3$, $SnCl_4$ or iodine. It is possible to cyclise the compounds of formula XI to compounds X i by dissolving the compounds to be cyclised in the presence of the acidic agent in an inert organic solvent. Most of the solvents commonly used, such as aliphatic cycloaliphatic or aromatic hydrocarbons or esters and ethers can be conveniently used. Preferably, acidic diatomaceous earth in dioxan or tetrahydrofuran is used.

As basic agents strong inorganic bases, such as hydroxy-derivatives of alkali metals, for example lithium, sodium or potassium hydroxides, or organic bases, such as primary, secondary or tertiary amines, for example diethylamine, triethylamine, n-propylamine, di-n-propylamine, tri-n-propylamine, n-butylamine, aniline, methylaniline, dimethylaniline, trimethylamine or diethylamine, can be used. In addition, said cyclisation can be carried out by means of usual nucleophilic reagents such as, for example, $I^-$, $SO_3^=$ or $S_2O_3^=$.

The bicyclic ketone of formula

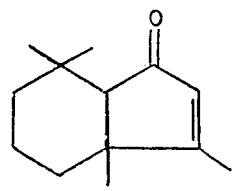

X a is also prepared by oxidising the corresponding carbinol having the formula

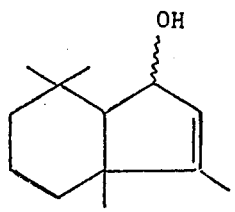

XV

Compound XV can be converted to Xa by means of the oxidising agents commonly used for oxidising a secondary alcohol in a ketone such as, for example, oxygen-containing derivatives of a transition metal such as chrome, manganese or nickel.

The starting carbinol which is a new compound can be obtained by isomerisation and simultaneous reduction of the epoxide XVI a

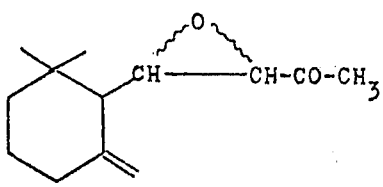

XVI a according to a procedure analogous to that followed for converting XVI into V γ-a [see above, cf. Tetrahedron 19, 1091 (1963) and J. Org. Chem. 26, 3615 (1961)].

According to another method of the invention, compounds of formula XII are prepared by cyclising by means of an acidic or basic agent compounds having the formula

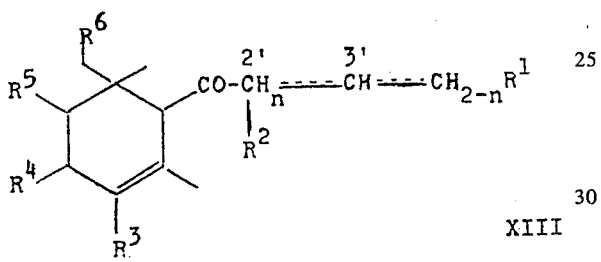

XIII containing one double bond in position 2'- or 3'- of the acyl side-chain, the double bond being represented by a dotted line, and wherein the symbols R have the same meaning as in formula XII and the index n is zero or 1.

The above cyclisation can be carried out by using the same type of acidic or basic reagents as those mentioned for converting compounds XI to their corresponding bicyclic derivatives Xi. Preferably, there is used, as cyclising agent, $BF_3$ in an inert organic solvent such as, for example, benzene, toluene or ether, or a mixture thereof.

The present invention describes also a method for the preparation of cyclic ketones of formula XIV which comprises cyclising by means of heat compounds of formula

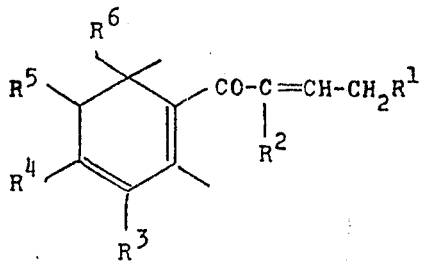

wherein the symbols R have the same meaning as in formula XIV.

The reaction can be carried out in inert organic solvents such as, for example, those already mentioned for the cyclisation of compounds XI or XIII. The temperature to which said cyclisation can occur is not critical. It is preferable to operate at a temperature comprised between 100° and 160°. At lower temperatures the reaction time can be considerably longer. At temperatures higher than those indicated the reaction time can be shorter; however, at these temperatures fragmentation reactions can occur.

Specific examples of compounds comprised by the various structural formulae shown hereinbefore include 2,4,6,6-tetramethyl-1-trans-crotonoyl-1-cyclohexene,
2,4,6,6-tetramethyl-1-[1-hydroxy-2-butenyl]-1-cyclohexene,
2,4,6,6-tetramethyl-1-trans-crotonoyl-1,3-cyclohexadiene,
2,5,6,6-tetramethyl-1-trans-crotonoyl-1-cyclohexene,
2,5,6,6-tetramethyl-1-[1-hydroxy-2-butenyl]-1-cyclohexene,
2,5,6,6-tetramethyl-1-trans-crotonoyl-1,3-cyclohexadiene,
2,5,6,6-tetramethyl-1-[3-methyl-2-butenoyl]-1-cyclohexene,
2,6,6-trimethyl-1-[1-hydroxy-3-methyl-2-butenyl]-1-cyclohexene,
2,6,6-trimethyl-1-[3-methyl-2-butenoyl]-1-cyclohexene,
2,6,6-trimethyl-1-[3-methyl-2-butenoyl]-1,3,-cyclohexadiene,
2,3,6,6-tetramethyl-1-crotonoyl-2-cyclohexene,
2,3,6,6-tetramethyl-1-[1-hydroxy-2-butenyl]-2-cyclohexene,
2,6,6-trimethyl-1-vinylacetate-1-cyclohexene,
2,6,6-trimethyl-1-[3-methyl-3-butenoyl]-1-cyclohexene,
2,6,6-trimethyl-1-[2-pentenoyl]-2-cyclohexene,
7,11-dimethyl-5-oxo-3,6,10-dodecatriene,
2,6,6-trimethyl-1-[2-methylcrotonoyl]-2-cyclohexene,
2,6,6-trimethyl-1-[3-methylcrotonoyl]-2-cyclohexene,
2,6,6-trimethyl-1-crotonoyl-1,2-epoxycyclohexane,
2,6,6-trimethyl-1-vinylacetyl-1,2-epoxycyclohexane,
2,6,6-trimethyl-1-[1-hydroxy-3-butenyl]-1-cyclohexene,
2,6,6-trimethyl-1-[1-hydroxy-3-butenyl]-1,2-epoxycyclohexane,
2,6,6-trimethyl-1-[1-hydroxy-2-butenyl]-1,2-epoxycyclohexane,
2,6,6-trimethyl-1-[1-hydroxy-3-butenyl]-2-cyclohexene,
2,6,6-trimethyl-1-vinylacetyl-2-cyclohexene,
2,6,6-trimethyl-1-hydroxy-1-crotonoyl-2-cyclohexene,
1,5,5,8,9-pentamethylbicyclo[4.3.0]non-8-en-7-one,
1,4,5,5,8,9-hexamethylbicyclo[4.3.0]non-8-en-7-one,
4,4,8-trimethyl-9-methylene-bicyclo[3.3.1]nonan-6-one,
1,5,5,9-tetramethylbicyclo[4.3.0]nona-2,8-dien-7-one,
1,5,5,9-tetramethylbicyclo[4.3.0]non-8-en-7-ol,
1,5,5,9-tetramethylbicyclo[4.3.0]non-8-en-7-one,
6,6-dimethyl-2-methylene-1-crotonoylcyclohexane,
2,6,6-trimethyl-1-[1-hydroxy-2-butynyl]-1-cyclohexene,
2,6,6-trimethyl-1-[1-hydroxy-2-butynyl]-2-cyclohexene, cis- and trans-2,6,6-trimethyl-1-[1-hydroxy-2-butenyl]-1-cyclohexene,
2,6,6-trimethyl-1-[1-hydroxy-2-butenyl]-2-cyclohexene,
6,10-dimethyl-4-oxo-2,5,9-undecatriene, cis- and trans-2,6,6-trimethyl-1-crotonoyl-1-cyclohexene,
cis- and trans-2,6,6-trimethyl-1-crotonoyl-2-cyclohexene,
trans-2,6,6-trimethyl-1-crotonoyl-1,3-cyclohexadiene,
2,6,6-trimethyl-1-tetrolyl-1-cyclohexene and
2,6,6-trimethyl-1-tetrolyl-2-cyclohexene.
cis- and trans-2,3,6,6-tetramethyl-1-[2-methyl-2-butenoyl]-1,3-cyclohexadiene,
2,3,6,6-tetramethyl-1-[3-methyl-2-butenoyl]-1,3-cyclohexadiene
cis- and trans-2,3,6,6-tetramethyl-1-[2-pentenoyl]-1,3-cyclohexadiene,
cis- and trans-2,3,6,6-tetramethyl-1-crotonoyl-1,3-cyclohexadiene,
cis- and trans-2,4,6,6-tetramethyl-1-[2-methyl-2-butenoyl]-1,3-cyclohexadiene,
2,4,6,6-tetramethyl-1-[3-methyl-2-butenoyl]-1,3-cyclohexadiene,
cis-2,4,6,6-tetramethyl-1-crotonoyl-1,3-cyclohexadiene,
cis- and trans-2,4,6,6-tetramethyl-1-[2-pentenoyl]-1,3-cyclohexadiene,
cis- and trans-2,5,6,6-tetramethyl-1-[2-methyl-2-butenoyl]-1,3-cyclohexadiene
2,5,6,6-tetramethyl-1-[3-methyl-2-butenoyl]-1,3-cyclohexadiene,
cis- and trans-2,5,6,6-tetramethyl-1-[2-pentenoyl]-1,3-cyclohexadiene,
cis-2,5,6,6-tetramethyl-1-crotonoyl-1,3-cyclohexadiene,
cis- and trans-2,6-dimethyl-6-ethyl-1-[2-methyl-2-butenoyl]-1,3-cyclohexadiene,
2,6-dimethyl-6-ethyl-1-[3-methyl-2-butenoyl]-1,3-cyclohexadiene
cis- and trans-2,6-dimethyl-6-ethyl-1-[2-pentenoyl]-1,3-cyclohexadiene,
cis- and trans-2,6-dimethyl-6-ethyl-1-crotonoyl-1,3-cyclohexadiene
cis- and trans-2,6,6-trimethyl-1-[2-methyl-2-butenoyl]-1,3-cyclohexadiene,
cis- and trans-2,6,6-trimethyl-1-[2-pentenoyl]-1,3-cyclohexadiene,
cis- and trans-2,3,6,6-tetramethyl-1-[2-methyl-2-butenoyl]-2-cyclohexene,
2,3,6,6-tetramethyl-1-[3-methyl-2-butenoyl]-2-cyclohexene,
cis- and trans-2,3,6,6-tetramethyl-1-[2-pentenoyl]-2-cyclohexene,
cis- and trans-2,4,6,6-tetramethyl-1-[2-methyl-2-butenoyl]-2-cyclohexene,
2,4,6,6-tetramethyl-1-[3-methyl-2-butenoyl]-2-cyclohexene,
cis- and trans-2,4,6,6-tetramethyl-1-[2-pentenoyl]-2-cyclohexene
cis- and trans-2,4,6,6-tetramethyl-1-crotonoyl-2-cyclohexene,
cis- and trans-2,5,6,6-tetramethyl-1-[2-methyl-2-butenoyl]-2-cyclohexene,
2,5,6,6-tetramethyl-1-[3-methyl-2-butenoyl]-2-cyclohexene,
cis- and trans-2,5,6,6-tetramethyl-1-1-[2-pentenoyl]-2-cyclohexene,
cis- and trans-2,5,6,6-tetramethyl-1-crotonoyl-2-cyclohexene,
cis- and trans-2,6-dimethyl-6-ethyl-1-[2-methyl-2-butenoyl]-2-cyclohexene,
2,6-dimethyl-6-ethyl-1-[3-methyl-2-butenoyl]-2-cyclohexene, cis- and trans-2,6-dimethyl-6-ethyl-1-[2-pentenoyl]-2-cyclohexene,
cis- and trans-2,6-dimethyl-6-ethyl-1-crotonoyl-2-cyclohexene,
cis- and trans-2,3,6,6-tetramethyl-1-[2-methyl-2-butenoyl]-1-cyclohexene,
2,3,6,6-tetramethyl-1-[3-methyl-2-butenoyl]-1-cyclohexene,
cis- and trans-2,3,6,6-tetramethyl-1-[2-pentenoyl]-1-cyclohexene,
cis- and trans-2,3,6,6-tetramethyl-1-crotonoyl-1-cyclohexene,
cis- and trans-2,4,6,6-tetramethyl-1-[2-methyl-2-butenoyl]-1-cyclohexene,
2,4,6,6-tetramethyl-1-[3-methyl-2-butenoyl]-1-cyclohexene,
cis- and trans-2,4,6,6-tetramethyl-1-[2-pentenoyl]-1-cyclohexene,
cis- and trans-2,5,6,6-tetramethyl-1-[2-methyl-2-butenoyl]-1-cyclohexene,
cis- and trans-2,5,6,6-tetramethyl-1-[2-pentenoyl]-1-cyclohexene
cis-2,5,6,6-tetramethyl-1-crotonoyl-1-cyclohexene,
cis- and trans-2,6-dimethyl-6-ethyl-1-[2-methyl-2-butenoyl]-1-cyclohexene,
2,6-dimethyl-6-ethyl-1-[3-methyl-2-butenoyl]-1-cyclohexene,
cis- and trans-2,6-dimethyl-6-ethyl-1-[2-pentenoyl]-1-cyclohexene,
cis- and trans-2,6,6-trimethyl-1-[2-methyl-2-butenoyl]-1-cyclohexene,
cis- and trans-2,6,6-trimethyl-1-[2-pentenoyl]-1-cyclohexene,
cis- and trans-3,6,6-trimethyl-2-methylene-1-[3-methyl-2-butenoyl]-cyclohexane,
cis- and trans-3,6,6-trimethyl-2-methylene-1-[2-pentenoyl]-cyclohexane,
cis- and trans-3,6,6-trimethyl-2-methylene-1-crotonoylcyclohexane,
cis- and trans-4,6,6-trimethyl-2-methylene-1-[2-methyl-2-butenoyl]-cyclohexane,
4,6,6-trimethyl-2-methylene-1-[3-methyl-2-butenoyl]-cyclohexane,
cis- and trans-4,6,6-trimethyl-2-methylene-1-[2-pentenoyl]-cyclohexane,
cis- and trans-4,6,6-trimethyl-2-methylene-1-crotonoylcyclohexane,
cis- and trans-5,6,6-trimethyl-2-methylene-1-[2-methyl-2-butenoyl]-cyclohexane,
5,6,6-trimethyl-2-methylene-1-[3-methyl-2-butenoyl]-cyclohexane,
cis- and trans-5,6,6-trimethyl-2-methylene-1-[2-pentenoyl]-cyclohexane,
cis- and trans-5,6,6-trimethyl-2-methylene-1-crotonoylcyclohexane,
cis- and trans-6-ethyl-6-methyl-2-methylene-1-[2-methyl-2-butenoyl]-cyclohexane,
6-ethyl-6-methyl-2-methylene-1-[3-methyl-2-butenoyl]-cyclohexane,
cis- and trans-6-ethyl-6-methyl-2-methylene-1-[2-pentenoyl]-cyclohexane,
cis- and trans-6-ethyl-6-methyl-2-methylene-1-crotonoylcyclohexane,
cis- and trans-6,6-dimethyl-2-methylene-1-[2-methyl-2-butenoyl]-cyclohexane,
6,6-dimethyl-2-methylene-1-[3-methyl-2-butenoyl]-cyclohexane,
cis- and trans-6,6-dimethyl-2-methylene-1-[2-pentenoyl]-cyclohexane, 2,6,6-trimethyl-1-[3-methyl-3-butenoyl]-2-cyclohexene and cis- and trans-2,6-dimethyl-6-ethyl-1-crotonoyl-1-cyclohexene.

The invention will be illustrated in a more detailed manner by the following Examples. In said Examples temperatures are given in degrees centigrade.

EXAMPLE 1

2,4,6,6-Tetramethyl-1-trans-crotonoyl-1-cyclohexene

A mixture of 10 g. of 2,4,6,6-tetramethyl-1-[1-hydroxy-2-butenyl]-1-cyclohexene, prepared according to paragraph (f) hereinafter, 100 g. of activated $MnO_2$ and 300 ml. of pentane was stirred at 20° in an atmosphere of argon during 45 h. After filtration the solid was washed with pentane and the clear filtrate was brought to dryness. The residue obtained from the above operation was dissolved in 100 ml. of dry benzene, added of 160 mg. of p-toluensulfonic acid and allowed to react at room temperature in argon atmosphere during 16 h. By extracting with ether in the presence of $NaHCO_3$ (5 % solution) and collecting the organic layers, 7.96 g. (80 %) of 2,4,6,6-tetramethyl-1-trans-crotonoyl-1-cyclohexene were obtained after distillation in vacuo. B. p. 60-2°/0.001 Torr.

Purification by column chromatography ($H_2SiO_3$, benzene) gave a pure sample; the analytical data were as follows: $d_4^{20} = 0.9223$; $n_D^{20} = 1.4919$; I.R.:$\nu=970$ (—CH=CH—trans), 1615, 1645, 1670 $cm^{-1}$ (C=C, C=O); Mass spectrum: $M^+ = 206$; NMR.: 0.80–1.05 (6 H, m, 2 $CH_3$—), 1.09 (3 H, s, $CH_3$—$\overset{|}{\underset{|}{C}}$—), 1.48 (3 H, s, $CH_3$—C=),
1.88 (3 H, d.d., J = 6.5 and ca. 1 cps, —CH=CH—$\underline{CH}_3$), 1.2–2.2 (5 H, m), 6.00 (1 H, d. q., J = 16 and ca. 1 cps, —CO—$\underline{CH}$=CH—$CH_3$), 6.63 (1 H, d. q., J = 16 and 6.5 cps, —CO—CH=$\underline{CH}$—$CH_3$), UV.: $\lambda_{max}$ = 225 m$\eta$($\epsilon^{EtOH}$ = 12,390)
$C_{14}H_{22}O$ Cal'ed C 81.50 H 10.75 %: Found C 81.49 H 10.89.

2,4,6,6-Tetramethyl-1-[1-hydroxy-2-butenyl]-1-cyclohexene used as starting material in the above preparation can be obtained as follows:

a. 4-Methyl-3-penten-2-ol according to Helv. Chim. Acta 30, 2216 (1947).

Mesityl oxide (245 g. dissolved in 1200 ml. of dry ether was added at reflux temperature to a mixture of $LiAlH_4$ (30 g.) in 200 ml. of the same solvent (1 h.). The mixture was allowed to react at 20° during 2 h. and after decomposition of the excess of $LiAlH_4$ by means of wet ether, it was added to a solution of 200 g. of $NH_4Cl$ in 1 l. of water.

After extraction with ether, the usual treatments gave 221 g. (88 %) of 4-methyl-3-penten-2-ol; B.p. 47°-50°/11 Torr. The product thus obtained was wet and it was conveniently dried by treatment with anhydrous $K_2CO_3$ in pet.-ether (30°–50°).

$d_4^{20} = 0.8421$; $n_D^{20} = 1.4388$; IR.: $\nu = 1050$ (C—O), 1670 (C=C), 3350 $cm^{-1}$ (OH); MS.: $M^+ = 100$; NMR.: 1.11 (3 H, d, J = 6 cps), 1.64 (6 H, m), 4.04 (1 H, s), 4.15–4.65 (1 H, m), 5.10 (1 H, d, J = ca. 8 cps). δ ppm.
$C_6H_{12}O$ Cal'ed: C 71.95; H 12.08 %; Found: C 71.83; H 12,19.

b. 4-Bromo-2-methyl-2-pentene according to Helv. Chim. Acta 30, 2216 (1947).

4-Methyl-3-penten-2-ol (220 g.) in 250 ml. of pet.-ether (30°–50°) and dry pyridine (41 g.) was added to a solution of freshly distilled $PBr_3$ (233 g.) and 10 drops of dry pyridine at −20° (1 h.). The reaction mixture was directly distilled and 274 g. (76 %) of 4-bromo-2-methyl-2-pentene were obtained. Owing to its instability, the product must be employed without too long storage.

c. 4,6-Dimethyl-5-hepten-2-one according to Helv. Chim. Acta 30, 2216 (1947).

The bromide (274 g.), obtained according to paragraph (b) hereinabove, was added at a temperature comprised between −5° and −10° to acetylacetate (obtained from 40.7 g. of sodium and 230 g. of ethyl acetylacetate) in 670 ml. of anhydrous ethanol. The reaction mixture was allowed to react during 2 days at 20° and, after the usual treatments of extraction and drying, 252 g. of the ketoester intermediate were obtained. This substance was dissolved in 928 ml. of ethanol, added to a solution of $Ba(OH)_2$ . 8 $H_2O$ (444 g in 3280 ml. of water), and kept to reflux during 2 h.

The precipitate which was formed during the above operation was dissolved with 10 % HCl, extracted with ether and subjected to the usual treatments.

142 g. (85 %) of product having B.p. 53°–7°/10 Torr were obtained. 70 % of this product was constituted by 4,6-dimethyl-5-hepten-2-one and 30 % by the allylic isomer.

The separation by means of preparative v.p.c. gave the two products which showed the following analytical data:

4,6-dimethyl-5-hepten-2-one

IR.: $\nu$ 830, 1360 ($CH_3CO$), 1710 $cm^{-1}$ (CO); MS.: $M^+ = 140$; NMR.: 0.89 (3 H, d, J = 6.5 cps), 1.62 (6 H, s), 2.00 (3 H, s), 2.22 (2 H, d, J = 7 cps.), 2.5–3.2 (1 H, m), 4.83 (1 H, d, J = 8 cps) δ ppm.

4,4-dimethyl-5-hepten-2-one

MS.: $M^+ = 140$ NMR.: 1.07 (6 H, s), 1.63 (3 H, d, J = 4.5 cps), 1.99 (3 H, s), 2.28 (2 H, s), 5.40 (2 H, m) δ ppm.

The mixture of these two isomers can be used as such in the following step. It must be noted that the rearranged structure will be eliminated during the successive cyclisation reaction (see paragraph e).

d. 2,4,6-Trimethyl-2,6-octadienal according to Tetrahedron Suppl. No. 8, Part I, 347 (1966).

Diisopropylamine (44.8 g.) in 100 ml. dry ether was added in an atmosphere of argon to a solution of butyllithium (14 % in hexane) in 200 ml. of dry ether and the mixture was then allowed to react at 20° during 2 h.

55 g. of ethylidencyclohexylamine were then added to the above mixture at 0°, followed by the addition at −70° of 70 g. of the ketones obtained according to paragraph c) above. The reaction mixture was left at −70° during 1½ h., then at 20° during one night. After addition of 800 ml. of 20 % acetic acid at 0°, stirring during 3 h. at 20° in an atmosphere of argon and extraction followed by the usual treatments, three fractions were obtained.

Fraction I: B.p. 30°–52°/0.01 Torr; 4.6 g.
Fraction II: B.p. 52°–70°/0.05 Torr; 44.6 g. (53 %)

Fraction III: B.p. 70°–80°/0.01 Torr; 5.1 g.
Residue 17 g.

Fraction II was redistilled and analysed by NMR. It was constituted by a mixture (ca. 3:2) of two isomeric aldehydes: 2,4,6-trimethyl-2,6-octadienal and 4,4,6-trimethyl-2,6-octadienal. This mixture was used for the next step.

e. 4-Methyl-β-cyclocitral

A mixture of the two isomeric aldehydes obtained according to paragraph d) (36.5 g.), aniline (21.4 g.) and anhydrous sodium sulphate (20 g.) in 55 ml. of ether was left at 20° under stirring during one night. After having filtered, washed and concentrated to the initial volume the solution was poured with vigorous stirring into 221 ml. of conc. $H_2SO_4$ and 22.1 g. of ice. The temperature was kept between −20° and −25° during 1 h., and the mixture was then added to 300 g. of ice and immediately distilled by means of steam distillation. The distillate was saturated with NaCl, extracted with ether and treated as usual. 36 g. of a mixture of crude α- and β- cyclocitral were thus obtained. The subsequent isomerisation was carried out at −10° in 120 ml. of a 8.5 % ethanolic KOH solution (80 % ethanol). The mixture was allowed to react during 3 h. in an atmosphere of argon, diluted then with pet.-ether (30° – 50°), poured into 400 ml. of a NaCl saturated aqueous solution and finally extracted with pet.-ether. By distillation 4 -methyl-β-cyclocitral was obtained:

Fraction I: B.p. 30°–73°/10 Torr; 1.4 g.
Fraction II: B.p. 90°–95°/10 Torr; 18.6 g. (51 %)
Residue 6 g.

$d_4^{20} = 0.9564$; $n_D^{20} = 1.4847$; IR: $\nu$ = 1610, 1670, 1720 (C=C; C=O), 2760, 2820 cm$^{-1}$ (CHO); MS: M$^+$ = 166; NMR: 0.92 (3 H, d, J = ca. 4 cps), 1.13 (6 H, s), 2.05 (3 H, s), 1.0–2.30 (5 H, m), 10.22 (1 H, s) δ ppm; UV: $\lambda_{max}^{EtOH}$ = 248 mη (ε = 9416) $C_{11}H_{18}O$ Cal.ed C 79.46; H 10.92 %; Found C 79.39; H 10.86.

f. 2,4,6,6-Tetramethyl-1-[1-hydroxy-2-butenyl]-1-cyclohexene

A solution of 16.4 g. of 4-methyl-β-cyclocitral obtained according to paragraph e) in 20 ml. dry ether was added (35 min.) at −20° to a solution of propenyl lithium. This latter solution was freshly prepared by adding at −10° a solution of 9.7 g. of 1-chloropropene in 80 ml. of dry ether to 1.85g. of granulated lithium containing 1 % of sodium. After being left 3 h. at 20° this lithium salt solution was ready for the addition of citral as described above.

After complete addition, the reaction was allowed to react at −15/−20° during 5 h., left at 20° during one night and poured then into 60 g. of NH$_4$Cl in water/ice. The reaction mixture was then extracted with ether and the ethereal combined extracts were concentrated at 40°–50° in vacuo, the product is thermolabile.

Fraction I: B.p. 30°–55°/0.001 Torr, 0.5 g.
Fraction II: B.p. 55°–8°/0.001 Torr, 18.6 g. (90 %)

Fraction II represents 2,4,6,6-tetramethyl-1-[1-hydroxy-2-butenyl]-1-cyclohexene in a cis- and trans-mixture.

$d_4^{20} = 0.9300$; $n_D^{20} = 1.4933$; IR: $\nu$ = 970 (-CH=CH-trans), 1030 (CO), 1645 (C=C), 3400 cm$^{-1}$ (OH); MS: M$^+$ = 208; NMR: 0.8–1.2 (9 H, m), 1.5–1.8 (6 H, m), 1.0–2.3 (5 H, m), 2.4 (1 H, s, wide band), 4.65 (1 H, m), 5.55 (2 H, m) δ ppm; $C_{14}H_{24}O$ Cal.ed C 80.71; H 11.61 %; Found C 80.71; H 11.48 %.

EXAMPLE 2

2,4,6,6-Tetramethyl-1-trans-crotonoyl-1,3-cyclohexadiene 2,4,6,6-Tetramethyl-1-trans-crotonoyl-1-cyclohexene (4.86 g.) obtained according to Example 1, was stirred at 50° with N-bromosuccinimide (5.85 g.), bis-azo-isobutyronitrile (0.6 mg.), 40 ml. of $CH_2Cl_2$ and 40 ml. of $CCl_4$ in a moisture-free vessel. After 50 min. the solution became clear due to the solution of NBS and succinimide precipitated. The mixture was stirred 5 min. more at 50° then, after cooling at 20°, diethylamine (10.6 g.) was added to it with stirring. After addition of 100 ml. of pet.-ether (30°–50°), homogenization and filtration, the filtrate gave by evaporation (at 40° under vacuum) and subsequent heating at 135°–145° during one hour, 3.60 g. (75 %) of a mixture 45:55 of the initial ketone and the final product. These two compounds were separated by v.p.c. (Carbowax 15 %, 200°, 2.5 m.).

2,4,6,6-Tetramethyl-trans-1-crotonoyl-1,3-cyclohexadiene can also be separated by column chromatography (40 parts by weight SiO$_2$ in the presence of benzene).

$d_4^{20} = 0.9431$, $n_D^{20} = 1.5115$, IR: $\nu$ = 970 (-CH=CH-trans), 1620–1670 cm$^{-1}$ (C=C, C=O); MS: M$^+$ =204; NMR: 1.00 (6 H, s), 1.60 (3 H, s), 1.89 (3 H, d.d., J = 6.5 and ca. 1 cps), 1.80 (3 H, s), ca. 1.7–1.9 (2 H, m), 5.52 (1 H, s wide), 6.05 (1 H, d, q., J = 16 and ca. 1 cps), 6.72 (1 H, d. q., J = 16 and 6.5 cps) δ ppm; UV: $\lambda_{max}^{EtOH}$ = 227 mη (ε = 15,090); $C_{14}H_{20}O$ Cal.ed C 82.30; H 9.87 %; Found C 82.43; H 10.09.

EXAMPLE 3

2,5,6,6-Tetramethyl-1-trans-crotonoyl-cyclohexene

A mixture of 8.0 g. of 2,5,6,6-tetramethyl-1-[1-hydroxy-2-butenyl]-1-cyclohexene, prepared according to paragraph e) hereinafter, 80 g. of activated MnO$_2$ and 250 ml of pentane was stirred at 20° in an atmosphere of argon during 21 h. After filtration the solid was thoroughly washed with pentane and the clear filtrate was brought to dryness. The residue thus obtained (8 g.), which was constituted by 81 % of the desired ketone, 16 % of its cis-isomer and 3 % impurity (v.p.c. Carbowax 15 %, 200°, 2.5 m.), was dissolved in 80 ml. of dry benzene, added of 160 mg. of p-toluensulfonic acid and allowed to react at room temperature in an atmosphere of argon during 16 h. By extracting with ether in the presence of NaHCO$_3$ (5 % solution) and collecting the organic layers, 6.83 g. (86 %) of 2,5,6,6-tetramethyl-1-trans-crotonoyl-1-cyclohexene were obtained by vacuum distillation, B.p. 64°–7°/0.001 Torr.

$d_4^{20} = 0.9426$; $n_D^{20} = 1.5016$; IR: $\nu$ = 970, 1615, 1640, 1670 cm$^{-1}$; MS: M$^+$ = 206; NMR: 0.8–1.0 (9 H, m); 1.47 (3 H, s); 1.87 (3 H, d.d., J = 6.5 and ca. 1 cps); 6.58 (1 H, d.q., J = 16 and 6.5 cps) δ ppm; UV: $\lambda_{max}^{EtOH}$ = 227 mη (ε = 11,545); $C_{14}H_{22}O$ Cal.ed C 81.50; H 10.75 %; Found C 81.27; H 10.46 %.

2,5,6,6-Tetramethyl-1-[1-hydroxy-2-butenyl]-1-cyclohexene used as starting material in the above preparation can be obtained as follows:

a. 1-Bromo-2,3-dimethyl-2-butene according to Helv. Chim. Acta 23, 964 (1940).

Hydrobromic acid (600 g., 30 % in acetic acid) was added under stirring to dimethylbutadiene (200 g.) at a temperature comprised between −25° and −15° during 1.5 h. After having been left 2 days at room temperature, the mixture was poured into ice-water and extracted with ether. The organic layer after the usual treatments gave two fractions:

Fraction I: B.p. 30°–40°/10 Torr, 60 g.
Fraction II: B.p. 42°–4°/10 Torr, 261 g. (72 %) of the desired product.
Residue, 50 g.

b. 5,6-Dimethyl-5-hepten-2-one according to Helv. Chim. Acta 23, 964 (1940).

The bromide (261 g.), obtained according to paragraph (a) hereinabove, was added at 6°–10° to acetyl acetate (obtained from 38.8 g. of sodium and 219 g. of ethylacetacetate) in 600 ml of anhydrous ethanol. The reaction mixture was allowed to react during one night at 20° and at reflux during 1.5 h. After dilution with 5-fold its volume of water and the usual treatments of extraction and drying, 263 g. (77 %) of the ketoester intermediate were obtained. The distillation gave also a fraction with B.p. 30°–42°/0.001 Torr, 35 g., and a residue of 0.5 g.

The ketoester was dissolved in 960 ml. of ethanol, added to a solution of $Ba(OH)_2.8H_2O$ (460 g. in 3400 ml. of water) and kept boiling during 22 h.

The precipitate which was formed during the above operation was dissolved with 10 % HCl, extracted with ether and subjected to the usual treatments.

144 g. (83 %) of a product having B.p. 70°–1°/10 Torr were obtained. Together with this product a fraction having B.p. 69°/10 Torr and a residue of 3.0 g. were obtained.

5,6-Dimethyl-5-hepten-2-one shows the following analytical constants:

$d_4^{20} = 0.8661$; $n_D^{20} = 1.4500$; IR: $\nu = 1350, 1710$ cm$^{-1}$; MS: M$^+$ =140; NMR:1.63 (9 H, s); 2.07 (3 H, s); 2.30 (4 H, m) δ ppm;

$C_9H_{16}O$ Calc.ed C77.09; H 11.50 % Found C 77.11; H 11.69 %.

c. 3,6,7-Trimethyl-2,6-octadienal according to Tetrahedron Suppl. No. 8, Part I, 347 (1966)

Methyl iodide (79.8 g.) in 250 ml. of dry ether was added at −15°, to a suspension of lithium (7.77 g) and 150 ml. of dry ether and the mixture was then allowed to react at 20° during 24 h.

Diisopropylamine (55.7 g.) in 100 ml. dry ether was added to the above mixture and left to react at 20° during 2 h.

68.7 g. of ethylidencyclohexylamine [see Bull. Soc. Chim. France 1947, 715] were added, followed by the addition at −70° of 70 g. of dimethylheptenone.

After the same treatment described in Example 1, paragraph d, 2 fractions were obtained:

Fraction I: B.p. 30°–53°10.001 Torr; 4.5 g.
Fraction II: B.p. 53°65°–69°/0.001 Torr; 46.1 g. (55 %)
Residue 28; g.

Fraction II is a mixture ca. 1:2 of cis- and trans-3,6,7,-trimethyl-2,6-octadienal which can be separated by v.p.c. (Carbowax, 15 %, 200°, 2.5 m.).

The mixture showed the following data:

$d_4^{20} = 0.8912$; $n_D^{20} = 1.4919$; IR: $\nu = 1630, 1660, 1715$ C=C, C=O), 2730, 2860 cm$^{-1}$ (CHO); MS M$^+$= 166; NMR 1.62 ( 9 H, s), 1.8–2.7 (7 H, complex band), 5.67 (1 H, d, J = 7.5 cps), 10.05 (1 H, almost $t$, J = 7.5 cps, due to mixing of two (d) δ ppm; $C_{11}H_{18}O$ Calc.ed C 79.46; H 10.92 %; Found C 79.21; H 10.80.

d. 5-Methyl-β-cyclocitral

A mixture of the two isomeric aldehydes obtained according to paragraph c) (38 g.), aniline (22.3 g.) and anhydrous sodium sulphate (20 g.) in 23 ml. of ether was treated as described in Example 1, paragraph e), using 230 ml. of conc. $H_2SO_4$ and 23 g. of ice.

After steam distillation, saturation with NaCl and extraation 32 g. (84 %) of a 2:3 mixture of 5-methyl-α-and 5 -methyl-β-cyclocitrals were obtained. The subsequent isomerisation was carried out at −10° in 120 ml. of a 8.5 % ethanolic KOH solution (80 % ethanol). By the treatment described in Example 2, e) 27.6 g. (86 %) of a product with B.p. 48°–54°/0.001 Torr were obtained. This product consists of 3–4 % of the α- and 96–7% of the β-isomer.

$d_4^{20} = 0.9528$; $n_D^{20} = 1.4990$; IR: $\nu = 1610, 1670, 1710, 2760, 2860$ cm$^{-1}$; MS: M$^+$= 166; NMR 0.89 (3 H, m); 1.03 (3 H, s); 1.18 (3 H, s); 2.08 (3 H, s); 1.2–2.4 (5 H, m); 10.27 (1 H, s) δppm; UV: $\lambda_{max}^{EtOH} = 248$ mη(ε = 10,546); $C_{11}H_{18}O$ Calc.ed C 79.46; H 10.92 %; Found C 79.43; H 10.80 %.

e. 2,5,6,6-Tetramethyl-1-[1-hydroxy-2-butenyl]-1-cyclohexene

A solution of 16.6 g. of 5-methyl-β-cyclocitral obtained according to paragraph d) hereabove in 20 ml. dry ether was added (35 min.) at −20° to a solution of propenyl lithium. This solution was freshly prepared according to Example 1, paragraph (f). The same treatment gave by distillation three fractions:

Fraction I; B.p. 40°–56°/0.001 Torr, 1.5 g.
Fraction II: B.p. 57°–62°/0.001 Torr, 1.3 g.
Fraction III: B.p. 64°–7°/0.001 Torr, 9.9 g. (47.5 %) of the desired product.

$d_4^{20} = 0.9656$; $n_D^{20} = 1.5055$; IR: $\nu = 970, 1670, 3400$ cm$^{-1}$; MS: M$^+$ = 208; NMR: 0.8–0.9 (3 H, m); 0.95 (6 H, s); 1.0–2.2 (12 H, m); 4.80 (1 H, s); 5.70 (2 H, m) ξ ppm; $C_{14}H_{24}O$ Calc.ed C 80.71; H 11.61 %; Found C 80.83; H 11.54 %.

EXAMPLE 4

2,5,6,6-Tetramethyl-1-trans-crotonoyl-1,3-cyclohexadiene 2,5,6,6-Tetramethyl-1-trans-crotonoyl-1-cyclohexene (4.86 g.), obtained according to Example 3, was allowed to react, according to the same procedure described in Example 2 for the preparation of the corresponding 2,4,6,6-tetramethyl derivative with N-bromosuccinimide (5.85 g.) bis-azo-isobutyronitrile (0.6 mg.), 40 ml. of $CH_2Cl_2$ and 40 ml. of $CCl_4$. By the usual treatment 3.71 g. (77 %) of a product at B.p. 75°/0.001 Torr were obtained.

$d_4^{20} = 0.9863$; $n_D^{20} = 1.5139$; IR: $\nu = 970, 1610, 1630, 1670$ cm$^{-1}$; MS: M$^+$ = 204; NMR: 0.89 (3H, s); 1.02 (3 H, s); 0.97 (3 H, d, J = ca. 8 cps); 1.58 (3 H, s); 1.88 (3 H, d. d., J = 6.5 and ca. 1 cps); 1.8–2.3 (1 H, m); 5.60 (2 H, m); 6.0 (1 H, d.q., J = 16 and ca. 1 cps); 6.70 (1 H, d.q., J = 16 and 6.5 cps) ε ppm; UV: $\lambda_{max}^{EtOH} = 228$ mη (ε = 11,640).

EXAMPLE 5

2,5,6,6-Tetramethyl-1-[3-methyl-2butenoyl]-1-cyclohexene 5-methyl-β-cyclocitral (11.0 g.) [cf. Example 3, paragraph d)] in 30 ml. THF was added at −10° to a Grignard solution obtained from 2.4 g. of magnesium and 13.5 g. of 1-bromo-2-methyl-propene in 30 ml. of dry tetrahydrofurane.

The reaction mixture was allowed to react during 2 h. at −5−0° and brought then at room temperature during one night.

The usual treatment with $NH_4Cl$ at 0° and extraction gave:

Fraction I: B.p. 40°/0.001 Torr; 1.3 g.

Fraction II: B.p. 70−2°/0.001 Torr; 8.7 g. (59 %) of the desired product.

Residue: 4 g.

IR: $\nu$ = 1020, 3400 cm$^{-1}$; MS: M$^+$ = 222; NMR: 0.65–1.10 (9 H, m); 1.6–2.0 (9 H); 2.45 (1 H, s); 1.0–2.2 (5 H, m); 4.9 (1 H; almost d, J = ca. 8 cps); 5.50 (1 H, almost d, J = ca. 8 cps) δ ppm.

The alcohol obtained above (6.4 g.) with $MnO_2$ (64 g.) in 190 ml. of pentane was left at 20° during 42 h. in an atmosphere of argon. The usual treatment [cf. Example 1] gave 5.3 g. of crude product. Two column chromatography runs, on 40 parts by weight of $H_2SiO_3$ and 24 parts by weight of $H_2SiO_3$ respectively, enabled to obtain pure 2,5,6,6-tetramethyl-1-[3-methyl-2-butenoyl]-1-cyclohexene.

B.p. 80°/0.001 Torr; $d_4^{20}$ = 0.9353; $n_D^{20}$ = 1.5040; IR: $\nu$ = 1605, 1665 cm$^{-1}$ MS: M$^+$ = 220; NMR: 0.80–1.10 (9 H, m); 1.53 (3 H, s); 2.14 (3 H, s); 1.39 (3H,s), 1.3–2.3 (5 H, m); 6.06 (1 H, s) δ ppm; UV: $\lambda_{max}^{EtOH}$ = 244 mη(ε = 13,510); $C_{15}H_{24}O$ Calc.ed C 81.76; H 10.98 %; Found: C 81.47; H 10.87.

EXAMPLE 6

2,6,6-Trimethyl-1-[1-hydroxy-3-methyl-2-butenyl]-1-cyclohexene

A solution of 1-chloro-2-methyl-propene (47.5 g.) in 50 ml. of dry ether was added at −10° (½ h) to a suspension of granulated lithium (7.6 g., containing 1% of sodium, in 50 ml. of dry ether) in an argon atmosphere.

The reaction mixture was allowed to react at room temperature during 3 h., then β-cyclocitral (63 g.) was added to it at −15°. After 5 more hours at that temperature the mixture was kept overnight at 20°, poured into a ice-cold aqueous solution of $NH_4Cl$ and finally extracted with ether.

After evaporation of the ether in vacuo at a temperature below 40°–50° (the product is thermolabile), 76 g. of crude alcohol were obtained. By carefufl distillation in the presence of traces of $Na_2CO_3$ two fractions were obtained:

Fraction I; B.p. 47°–55°/0.001 Torr, 16.1 g.

Fraction II: B.p. 55°–60°/0.001 Torr, 21.4 g. (24.8 %) of the desired product.

Fraction II solidified by cooling and was recrystallised with pet.-ether (30°–50°) at −10°.

M.p. 55°–56.5°; MS: M$^+$ = 208; IR: 1020, 1650, 3400–3600 cm$^{-1}$ NMR: 0.87 (3 H, s), 1.13 (3 H, s), 1.70–1.80 (9 H, m), 1.20 – 2.30 (6 H, m), 3.27 (1 H, s), 4.85 (1 H, d, J = 8cps), 5.46 (1 H, almost d, J = 8 cps) δ ppm. $C_{14}H_{24}O$ Calc.ed C 80.71; H 11.61 %; Found C 80.65; H 11.54 %.

EXAMPLE 7

2,6,6-Trimethyl-1-[3-methyl-2-butenoyl]-1-cyclohexene 2,6,6-Trimethyl-1[1-hydroxy-3-methyl-2-butenyl]-1-cyclohexene, prepared according to Example 6, (1.0 g.) with activated $MnO_2$ (10 g.) in 30 ml. of pentane was mixed at room temperature during 63 h. after filtration and distillation 630 mg. (63 %) of the desired ketone, B.p. 67°/0.001 Torr, were obtained.

$d_4^{20}$ = 0.9310; $n_D^{20}$ = 1.5029; IR: $\nu$ = 1605, 1665 cm$^{-1}$. MS: M$^+$ = 206; NMR: 1.04 (6 H, s), 1.55 (3 H, s), 1.89 (3 H, d, J = ca. 1 cps), 2.15 (3 H, s), 1.20–2.20 (6 H, m), 6.09 (1 H, s) δ ppm; UV: $\lambda_{max}^{EtOH}$ = 244 mη (ε = 12,840); $C_{14}H_{22}O$ Calc.ed C 81.50; H 10.75 %; Found C 81.27; H 10.77.

EXAMPLE 8

2,6,6-Trimethyl-1-[3-methyl-2-butenoyl]-1,3-cyclohexadiene

Under anhydrous conditions 2,6,6-trimethyl-1-[3-methyl-2-butenoyl]-1-cyclohexene (2.1 g.) was heated to 45°–50° in the presence of N-bromosuccinimide (2.18 g.) in 20.4 ml. of $CH_2Cl_2$ and 20.4 ml. of $CCl_4$. The reaction mixture was allowed to react until complete precipitation of succinimide (1 h.).

Diethylamine (3.46 ml.) was added to the above mixture at 20° followed by 51 ml. of pet.-ether (30°–50°). After filtration and evaporation (40°) of the clear filtrate, the residual product was heated at 130°–150° in an atmosphere of argon during 1 h., and, after cooling, poured into, an excess of 10 % HCl in the presence of pet.-ether and finally extracted with more pet.-ether.

1.38 g. (66 %) of a product with B.p. 70°/0.001 Torr were obtained. This fraction was constituted by a 1:1 mixture of starting material and final product. Column chromatography (silicic ac. in the presence of benzene) gave a pure product:

$d_4^{20}$ = 0.9566; $n_D^{20}$ = 1.5169; IR: $\nu$ = 1602, 1660 cm$^{-1}$; MS: M$^+$ = 204; NMR: 1.03 (6 H, s), 1.67 (3 H, s), 1.85 (3 H, d, J = ca. 1 cps), 2.02 (2 H, s), 6.01 (1 H, s), δ ppm; $\lambda_{max}^{EtOH}$ = 246 mη (ε = 12,490); 309 mη (ε = 2980). $C_{14}H_{20}O$ Calc.ed C 82.30; H 9.87 %; Found: C 82.15; H 10.12.

EXAMPLE 9

2,3,6,6-Tetramethyl-1-crotonoyl-2-cyclohexene 2,3,6,6-Tetramethyl -1-[1-hydroxy-2-butenyl]-2-cyclohexene (8.4 g.), obtained according to paragraph (e) of this Example, was oxidised and isomerised according to the same procedure described in Example 1.

The product obtained after purification by means of column chromatography (silicic acid, benzene) was constituted by 1.31 g. (15.7 %) of the desired ketone.

$d_4^{20}$ = 0.9330; $n_D^{20}$ = 1.4976; IR: $\nu$ = 970, 1620–1680 cm$^{-1}$; MS: M$^+$ = 206; NMR: 0.80 (3 H, s), 0.90 (3 H, s), 1.50 (3 H, s), 1.55 −2.40 (10 H, complex band), 2.82 (1 H, s), 6.19 (1 H, d.q., J = 16 and ca. 1 cps), 6.80 (1 H, d.q., J = 16 and 6.5 cps), δ ppm; UV: $\lambda_{max}^{EtOH}$ = 227 mη (ε = 10,810); $C_{14}H_{22}O$ Calc.ed C 81.50; H 10.75 %; Found C 81.81; H 11.00.

The carbinol used as starting material in the above preparation can be prepared as follows:

1-Bromo-3-methyl-butene according to Helv. Chim. Acta 5, 750 (1922)

A 30 % solution of hydrobromic acid (815 g.) in acetic acid were added (1.5 h.) ar −20° to 200 g. of isoprene and the resulting mixture was kept 3 days at 0°, poured into 4 l. of cold water, decanted, dried over $CaCl_2$ and distilled to give the desired bromide. B.p. 24–8°/10 Torr, 312 g. (71 %).

3,6-Dimethyl-5-hepten-2-one according to Helv. Chim. Acta 30, 2213 (1947).

According to a procedure analogous to that described in paragraph c) of Example 1, the bromide obtained above (312 g.) was added at a temperature comprised between −5° and −10° to acetylacetate (obtained from 38.5 g. of sodium and 250 g. of ethyl α-Methyl acetylacetate) in 940 ml. of ethanol. The reaction mixture was allowed to react during 2 days at 20° and, after the usual treatments of extraction and drying (cf. Example 1, paragraph c) two fractions were obtained:

Fraction I: B.p. 41–65°/0.001 Torr, 168 g.
Fraction II: B.p. 65–70°/0.001 Torr, 219 g. (61 %) of the ketoester intermediate.
Residue: 17 g.

160 g. of the product of fraction II were brought to the boil with $Ba(OH)_2.8 H_2O$ (307 g.) in 2130 ml. of water and 665 ml. of ethanol during 22 h. After the same treatment as in paragraph (c) of Example 1, two fractions were obtained:

Fraction I: B.p. 30°–55°/8 Torr, 2.3 g.
Fraction II: B.p. 55°–8°/8 Torr, 79.6 g. (75 %) of the desired 3,6-dimethyl-5-hepten-2-one:

$d_4^{20} = 0.8495$; $n_D^{20} = 1.4414$; IR: $\nu = 1350, 1710$ cm$^{-1}$; MS: M$^+ = 140$; NMR: 1.00 (3 H, d, J = 6.5 cps); 1.58 (3 H, s); 1.66 (3 H, s); 2.03 (3 H, s); 1.7–2.7 (3 H, m); 5.00 (1 H, t, J = 7 cps) δ ppm; $C_9H_{16}O$ Calc.ed C 77.09; H 11.50 %; Found C 76.81; H 11.40.

c. 3,4,7-Trimethyl-2,6-octadienal according to Tetrahedron Suppl. No. 8, Part 1, 347 (1966).

Diisopropylamine (56.1 g.) in 100 ml. dry ether were added under argon to a solution of butyl-lithium (275 g. of a 14 % solution in hexane) in 200 ml. of dry ether and the mixture was then allowed to react at 20° during 2 h.

68.7 g. of ethylidencyclohexylamine were added to 70 g. of the ketone obtained according to paragraph (b) of this Example [cf. Example 1, paragraph d)]. The distillation gave:

Fraction I: B.p. 30°–52°/0.001 Torr, 0.8 g.
Fraction II: B.p. 52°–62°/0.001 Torr, 57 g. (68 %) of the desired product.
Residue: 22 g.

$d_4^{20} = 0.8883$; $n_D^{20} = 1.4866$; IR: $\nu$ 1620, 1670, 1710 cm$^{-1}$; MS: M$^+ = 166$; NMR: 1.06 (3 H, d, J = 6 cps); 1.57 (3 H, s); 1.65 (3 H, s); 2.08 (3 H, s); 1.8–2.5 (3 H, m); 4.95 (1 H, t, J = ca. 7 cps); 5.68 (1 H, d, J = 7.5 cps); 9.79 (1 H, d, J = 7.5 cps) δ ppm; UV: $\lambda_{max}^{EtOH} = 241$ mη ($\epsilon = 14,250$); $C_{11}H_{18}O$ Calc.ed C 79.46 ; H 10.92 %; Found C 78.41 ; H 10.89.

d. 3-Methyl-α-cyclocitral

The usual cyclisation procedure (cf. Example 1, paragraph e) gave 36 g. of 3-methyl-α-cyclocitral from 46.6 g. of 3,4,7-trimethyl-2,6-octadienal. The obtained α-cyclocitral contained 12 % of the β-isomer:

Fraction I: B.p. 70°–8°/8 Torr, 4 g.
Fraction II: B.p. 81°–3.5°/8 Torr, 20.6 g.
Fraction III: B.p. 84°/8 Torr, 1.4 g.
Residue: 7 g.

Reaction II (yield 44 %) contains 91 % of 3-methyl-α-cyclocitral, 7 % of the corresponding β-isomer and 2 % of unknown impurity.

$d_4^{20} = 0.9256$; $n_D^{20} = 1.4805$ IR: $\nu = 1670, 1710, 2710, 2860$ cm$^{-1}$. MS: M$^+ = 166$; NMR: 0.87 (3 H, s); 0.95 (3 H, s); 1.52 (3 H, s); 1.68 (3 H, s); 1.0–2.4 (5 H, m); 9.28 (1 H, d, J = 5 cps) δ ppm. $\lambda_{max}^{EtOH} = 238$ mη ($\epsilon = 2850$); $C_{11}H_{18}O$ Calc.ed C 79.46; H 10.92 %; Found C 79.41; H 10.91.

2,3,6,6-Tetramethyl-1-[1-hydroxy-2-butenyl]-2-cyclohexene

3-Methyl-α-cyclocitral (20.5 g.), lithium (2.29 g.) and 1-chloropropene (11.9 g.) were allowed to react in 125 ml. of dry ether according to the same procedure described in paragraph f of Example 1. The distillation gave:

Fraction I: B.p. 30°–50°/0.001 Torr; 1.0 g.
Fraction II: B.p. 56°–9°/0.001 Torr; 16.8 g. (65 %) of the desired carbinol.
Residue: 4 g.

The product of fraction II was used directly for the preparation of the corresponding ketone.

EXAMPLE 10

2,6,6-Trimethyl-1-crotonyl-1-cyclohexene 2,6,6-Trimethyl-1-vinylacetyl-1-cyclohexane (10 g.) was heated at 80° during 30 minutes with p-toluensulfonic acid (0.2 g.) and benzene (100 ml.) After cooling, the solution was neutralised with a concentrated aqueous solution of $Na_2CO_3$, washed with water, dried and distilled according to the usual procedure. Trans-2,6,6-trimethyl-1-crotonoyl-1-cyclohexene, B.p. 84°–5°/0.001 Torr; $d_4^{20} = 0.9374$; $n_D^{20} = 1.4989$.

2,6,6-Trimethyl-1-vinylacetyl-1-cyclohexene, used as starting material in the above preparation, was prepared as described in Example 11.

EXAMPLE 11

2,6,6-Trimethyl-1-vinylacetyl-1-cyclohexene and 2,6,6-trimethyl-1-[3-methyl-3-butenoyl]-1-cyclohexene (cf. J. Am. Chem. Soc., 75, 422 (1953)).

At 0° and with vigorous stirring pure chromic anhydride (41 g.) was added portion-wise to 450 ml. of dry pyridine. To this solution 2,6,6-trimethyl-1-[1-hydroxy-3-butenyl]-1-cyclohexene (44.5 g.) in 80 ml. pyridine was then added dropwise at 0°. The reaction mixture was kept at this temperature during 30 minutes and allowed then to stand at 20° for 10 hours.

The solution was poured into 1 l. of water and extracted with ether. The combined extracts were washed with a 10 % aqueous HCl solution, neutralised with a 5 % aqueous solution of $Na_2CO_3$ and finally washed with water. After the usual treatments followed by distillation, 2,6,6-trimethyl-1-vinylacetyl-1-cyclohexane (60 % yield) was obtained. $n_D^{20} = 1.4897$; $d_4^{20} = 0.9361$.

By replacing hereabove 2,6,6-trimethyl-1-[1-hydroxy-3-butenyl]-1-cyclohexene with 2,6,6-trimethyl-1-[1-hydroxy-3-methyl-3-butenyl]-1-cyclohexene ($n_D^{20} = 1.4939$; $d_4^{20} = 0.9270$), 2,6,6-trimethyl-1-[3- methyl-3-butenoyl]-1-cyclohexene was obtained; $n_D^{20}$ = 1.4862; $d_4^{20}$ = 0.9307.

The hydroxylic compounds used as starting material in the above described preparation, have been prepared according to the usual conditions by a Grignard reaction between β-cyclocitral and allyl bromides or between β-cyclocitral and methallyl chloride.

In a typical experiment 10.7 g. of Mg turnings and 5 g. of allyl bromide were allowed to react in 70 ml. of dry ether. The reaction was exothermic and the temperature of the reaction mixture increased up to the boiling point of the solvent. To this solution allyl bromide (46 g.) and β-cyclocitral (61 g.) in 160 ml. of ether were added with vigorous stirring at such a rate as to maintain the ether at the boiling temperature. The reaction mixture was then kept at reflux during 6 hours and after cooling it was poured into a ice-cold concentrated aqueous solution of $NH_4Cl$. The ethereal layer after the usual treatments gave 2,6,6-trimethyl-1-[1-hydroxy-3-butenyl]-1-cyclohexene (44.5 g.; 57 % yield): B.p. 60°–2°/0.001 Torr; $n_D^{20}$ = 1.4964; $d_4^{20}$ = 0.9398; NMR spectrum ($CCl_4$): 0.98 (3 H, s); 1.10 (3 H, s); 1.82 (3 H, s); 1.20–2.80 (9 H, m); 4.22 (1 H, m); 5.04 (2 H, d, J = 15 cps); 5.88 (1 H, m) δ ppm.

By replacing in the above described preparation, allyl bromide with an equivalent of methallyl chloride, the corresponding carbinol was obtained with similar yields.

EXAMPLE 12

Trans-2,6,6-trimethyl-1-crotonyl-cyclohexene 17.6 g. of activated magnesium chips were suspended in 210 ml. of absolute tetrahydrofuran under nitrogen. Then a solution of 87.4 g. of 1-bromopropene in 50 ml. of absolute tetrahydrofuran was added dropwise at such a rate that the temperature was maintained between 40° and 45°.

When the addition of the bromine derivative was completed, the mixture was refluxed for 45 minutes; then cooled to −10°, at which temperature 110 g. of β-cyclocitral dissolved in 410 ml. of tetrahydrofuran were introduced dropwise within 45 minutes. Stirring was continued for 1 hour at −5°, then overnight at room temperature under nitrogen. The reaction mixture was poured into a suspension of 0.5 kg. of crushed ice in 1.5 l. of a saturated ammonium chloride solution. It was extracted 3 times with ether, the extracts were combined and washed 3 times with water and then with a concentrated NaCl solution. After drying over anhydrous $Na_2SO_4$ the volatile portions were evaporated and the residue distilled. There were thus obtained 91 g. (65.2 %) of cis-2,6,6-trimethyl-1-[1-hydroxy-2-butenyl]-1-cyclohexene. B.p. 64°–68°/0.01 Torr. By replacing in the above procedure the β-cyclocitral by its analogue α, cis-2,6,6-trimethyl-1-[1-hydroxy-2-butenyl]2-cyclohexene was obtained. 1700 ml. of absolute pyridine were cooled to 0°–5° and 154 g. of $CrO_3$ were added portionwise within 30 minutes while stirring vigorously. Stirring was continued for 10 minutes at 5° and then 95 g. of cis-2,6,6-trimethyl-1-[1-hydroxy-2-butenyl]-1-cyclohexene dissolved in 300 ml. of pyridine were added dropwise within 20 minutes, while maintaining the temperature below 10°. When the addition was completed stirring was continued for 20 minutes, then the mixture was allowed to stand for 15 hours at room temperature. The reaction mixture was diluted with 5 l.of water and extracted with 6 portions of 800 ml. of ether each. The extracts were combined and successively washed with: 4 portions of water, 8 portions of 10 % HCl at 0°, 3 portions of water, 2 portions of 5 % $Na_2CO_3$, 2 portions of water. Moreover, each washing portion was extracted with ether before being discarded, and the extract was added to the main extract after washing. The ethereal solution was dried over anhydrous $Na_2SO_4$, concentrated in vacuo and the residue distilled. There were thus obtained 57 g. of a liquid fraction, b.p. 75°–85°/0.001 Torr, which fraction was redistilled by means of a spinning band column and yielded 24 g. (25.5 %) of pure trans-2,6,6-trimethyl-1-crotonoyl-1-cyclohexene.

Analysis: Calc. for $C_{13}H_{20}O$ C 81.2 % H 10.48 % Found C 81.06 H10.42; $d_4^{20}$ = 0.9378 $n_D^{20}$ = 1.4989; IR spectrum: 1675, 1640, 1618, 972 cm$^{-1}$; NMR spectrum: δ = 0.98 ppm, (6 H, s); 1.48 ppm (3 H, s); 1.89 ppm, (3 H, d of d, J = 6.5 cps and 1.2 cps); 1.2–2.1 ppm, (6 H, complex band); 6.0 ppm, (1 H, d of q, J = 15 cps and 6.5 cps). Mass spectrum: m/e = 177, 69, 123, 192.

By replacing in the above procedure cis-2,6,6-trimethyl-1-[1-hydroxy-2-butenyl]-1-cyclohexene by cis-2,6,6-trimethyl-1-[1-hydroxy-2-butenyl]-2-cyclohexene, trans-2,6,6-trimethyl-1-crotonoyl-2-cyclohexene was obtained which had the following characteristics:

NMR spectrum: δ = 0.83 ppm, (3 H, s); 0.92 ppm, (3 H, s); 1.55 ppm, (3 H, s broad); 1.89 ppm, (d of d, J = 6.5 and 1.1 cps); 1.0–2.3 ppm (4 H, complex band); 2.77 ppm, (1 H, s broad); 5.52 ppm, (1 H, s broad); 6.18 ppm, (1 H, d of q, J = 16 cps and 1.1 cps); 6.77 ppm, (1 H, d of q, J = 16 cps and 6.5 cps).

EXAMPLE 13

Cis-2,6,6-trimethyl-1-crotonoyl-1-cyclohexene

To 80 ml. of pentane were added 15 g. of active $MnO_2$ and 1.6 g. of 2,6,6-trimethyl-1-[1-hydroxy-2-butenyl ]-1-cyclohexene prepared according to Example 12. The mixture was stirred for 5 days at room temperature and then filtered. The precipitate was rinsed several times with pentane and the rinsing fractions were added to the mother liquor. After concentration in vacuo, the residue was distilled to obtain 1.1 g. (68.6 %) of cis-2,6,6-trimethyl-1-crotonoyl-1-cyclohexene, b.p. 82°–85°/0.001 Torr. The analysis of the product yielded similar results as those obtained for Example 12. The constants were the following:

IR spectrum: 1665, 1640, 1605 cm$^{-1}$. Mass spectrum: m/e 177, 192, 123, 69. NMR spectrum: δ = 1.03 ppm, (6 H, s); 1.55 ppm, (3 H, s); 2.1 ppm, (3 H, d, J = 5.5 cps); 1.2–2.1 ppm, (6 H, complex band); 6.08 ppm, (2 H, complex band).

By replacing above 2,6,6-trimethyl-1-[1-hydroxy-2-butenyl]-1-cyclohexene by 2,6,6-trimethyl-1-[1-hydroxy-2-butenyl]-2-cyclohexene, cis-2,6,6-trimethyl-1-crotonoyl-2-cyclohexene was obtained.

EXAMPLE 14

Trans-2,6,6-trimethyl-1-crotonoyl-1,3-cyclohexadiene

The following mixture was stirred for 24 hours at room temperature: 1 g. of trans-2,6,6-trimethyl-1-crotonoyl-1-cyclohexene, 0.55 g. of $NaHCO_3$, 0.44 g. of CaO and 1.17 g. of N-bromosuccinimide in 7 ml. of $CCl_4$.

1.7 ml. of diethylaniline was added, the mixture was diluted with 2 volumes of petroleum ether (b.p.

30°–50°), filtered and the volatile portions were eliminated in vacuo (temperature < 50°). Then it was heated for 2 hours on the water-bath under nitrogen, whereupon it was allowed to cool. 0.57 ml. of pyridine were added and it was heated for 1 hour on the water-bath. It was cooled to 0° and diluted with a cold 10 % HCl solution until a distinctly acid mixture was obtained. It was extracted with 2 portions of petroleum ether (b.p. 30°–50°) and the extracts were washed in the following manner: 10 % HCl (at 0°), 5 % NaHCO$_3$, water. After drying over anhydrous Na$_2$SO$_4$ it was concentrated and the residue distilled under a high vacuum. There was thus obtained 0.31 g. (31.3 %) of trans-2,6,6-trimethyl-1-crotonoyl-1,3-cyclohexadiene. The analytical sample, purified by preparative gas chromatography had the following physical constants:

IR spectrum: 1670, 1635, 1610, 970 cm$^{-1}$. Mass spectrum: m/e: 69–121, 105, 41, 190. NMR spectrum: $\delta$ = 1.01 ppm, (6 H, s); 1.62 ppm, (3 H, s); 1.93 ppm, (3 H, d of d, J = 6.5 cps and 1.5 cps); 2.07 ppm, (2 H, d, J = 2.3 cps); 5.77 ppm, (2 H, t, J = 2.3 cps); 6.06 ppm, (1 H, d of q, J = 16 cps and 1.5 cps); 6.75 ppm, (1H, d of q, J = 16 cps and 6.5 cps).

EXAMPLE 15

Trans-2,6,6-trimethyl-1-crotonoyl-2-cyclohexene

A solution containing 2.8 g. of epoxy-α-ionone (Helv. Chim. Acta 29, 1829 (1946) in 15 ml. of absolute methanol was cooled and 2.5 g. of hydrazine hydrate were added under nitrogen with stirring, followed by 0.3 g. of acetic acid. The temperature was maintained between 10 and 20° and an evolution of nitrogen was observed. When the evolution of nitrogen was finished, the solution was diluted with water, neutralised and extracted by the usual means. After drying and evaporation of the volatile portions the extract yielded 2.4 g. of an oily liquid which was subjected to a fractional distillation. The second fraction of the distillation contained a 1:1 mixture of cis- and trans-2,6,6-trimethyl-1-[1-hydroxy-2-butenyl]-2-cyclohexene. 100 mg. of this distillate were dissolved in 15 ml. of acetone and this mixture was stirred for 60 hours at room temperature with 2 g. of MnO$_2$. The mixture was filtered and the precipitate rinsed twice with ether. After concentration of the solution and the rinsing fractions in vacuo a mixture of cis- and trans-2,6,6-trimethyl-1-crotonoyl-2-cyclohexene was obtained which was purified by preparative gas chromatography. The two isomeric ketones were thus separated and the constants thereof were identical to those described in Examples 20 hereinafter and 12 respectively.

EXAMPLE 16

2,6,6-Trimethyl-1-crotonoyl-1-cyclohexene a. 426 g. of 2,6,6-trimethyl-1-[1-hydroxy-2-butenyl]-1-cyclohexene prepared according to the method described in paragraph b herebelow were mixed with 3.9 kg. of MnO$_2$ in 8 liter of petroleum-ether (b.p. 30°–50°). The mixture was stirred for 2½ days at room temperature. The solvent was removed under vacuum and the crude 2,6,6-trimethyl-1-crotonoyl-1-cyclohexene (358 g.) which was left as the residue of evaporation was used without further purification. The crude ketone which was mainly the cis-isomer, according to the vapour phase chromatographic analysis was isomerised to the trans-ketone by means of p-toluensulfonic acid according to the process described in Example 19 hereinafter. After isomerisation the resulting trans-ketone was purified by fractional distillation, b.p. 84°–85°/0.001 Torr.

The carbinol used as starting material in the preparation described above can be prepared as follows:

b.
2,6,6-Trimethyl-1-[1-hydroxy-2-butenyl]-1-cyclohexene

In an atmosphere of nitrogen, a solution of 280 g. of 1-bromopropene in 430 ml. of tetrahydrofuran was added dropwise at 63°–65° into a suspension of 53.3 g. of magnesium turnings in 660 ml. of tetrahydrofuran. During the addition the reflux condenser fitting the reaction vessel was cooled to −40° to −50° in order to prevent escaping of the vapours of unreacted 1-bromopropene. The mixture was stirred for an additional 2½ hours at 60°–62° after which it was cooled to 0°. A solution of 278 g. of β-cyclocitral in 350 ml. of tetrahydrofuran was then added dropwise between 0° and 7°. The mixture was allowed to stand overnight then it was poured onto a mixture of ice and saturated aqueous NH$_4$Cl solution. The organic layer was removed and the aqueous phase extracted with petroleum-ether (b.p. 30°–50°). The combined extracts were washed as usual, dried and then evaporated under vacuum. The residue gave 350 g. of crude 2,6,6-trimethyl-1-[1-hydroxy-2-butenyl]-1-cyclohexene which was used without further purification.

EXAMPLE 17

2,6,6-Trimethyl-1-crotonoyl-1,3-cyclohexadiene

The following ingredients were stirred at 51°–53° under an atmosphere of nitrogen: 2,6,6-trimethyl-1-crotonoyl-1-cyclohexene prepared according to Example 16 (50 g.), N-bromosuccinimide (60.5 g.), CCl$_4$ (400 ml.), CH$_2$Cl$_2$ (200 ml.) and α,α'-azo-bis-isobutyronitrile (0.2 g.). The mixture turned progressively red and started abruptly to boil violently. The heat source was removed and the reaction rate was controlled by means of a cooling bath. After about 10 minutes the reaction mixture became colourless. It was cooled to 20° and 89.5 g. of diethylamine and 800 ml. of petroleum-ether (b.p. 30°–50°) were added to it. Succinimide was filtered off, volatile solvents were removed under vacuum and the residue was heated to 135°–140° for 2½ hours. After cooling, the mixture was stirred vigorously with 500 ml. of ice-cold 10 % HCl. The mixture was extracted with petroleum ether and the extract was washed with 5 % HCl, concentrated aqueous NaHCO$_3$ and finally with water. After drying over Na$_2$SO$_4$ the extract was distilled to give 37 g. (75 %) of pure 2,6,6-trimethyl-1-crotonoyl-1,3-cyclohexadiene b.p. 46°/0.001 Torr.

EXAMPLE 18

Cis-2,6,6-trimethyl-1-crotonoyl-1-cyclohexene a. A solution of 2,6,6-trimethyl-1-tetrolyl-1-cyclohexene prepared according to the description of paragraph c) herebelow (5 g.) in 50 ml. of petroleum-ether (b.p. 30°–50°) and 2 g. of Lindlar catalyst (deactivated Pd/C catalyst) prepared according to Helv. Chim. Acta 35, 446 (1952) were placed in an apparatus for catalytic hydrogenations. The above mixture was hydrogenated at room temperature until 1 equivalent of hydrogen had been used. The solution was filtered and the solvent removed in vacuo. Distillation of the residue gave 4.3 g. of cis-2,6,6-trimethyl-1-crotonoyl-1-cyclohexene, b.p. 82°–85°/0.001 Torr the constants of which were the same as those described in Example 13.

The acetylenic ketone used as starting material in the above preparation was prepared as follows:

b. 2,6,6-Trimethyl-1-[1-hydroxy-2-butynyl]-1-cyclohexene

Under an atmosphere of nitrogen 56 mMole of methyllithium in about 30 ml. of ether were added to 100 ml. of dioxane. The mixture was stirred vigorously and, between 0° and 10°, 2.47 g. (61.6 mMole) of propyne were added to it. The vapours of the propyne which did not immediately react were condensed in a condenser cooled with liquid nitrogen. The unreacted propyne was thus continuously returned to the reaction vessel. When all propyne had reacted (approx. 30–60 minutes) a solution of 7.6 g. (50 mMole) of β-cyclocitral in 10 ml. of ether was added dropwise at room temperature. After stirring for an additional 10–12 hours the mixture was poured onto ice, neutralised with $NH_4Cl$ and extracted with petroleum-ether. The extract was washed and dried by usual means, then it was concentrated under reduced pressure. Distillation of the residue gave 6.6 g. of 2,6,6-trimethyl-1-[1-hydroxy-2-butynyl]-1-cyclohexene, b.p. 95°–97°/0.7 Torr, as a colourless viscous oil.

c. Oxidation 2,6,6-trimethyl-1-[1-hydroxy-2-butynyl-]-1-cyclohexene

A mixture of 1.277 g. (66.3 mMole) of the acetylenic carbonyl compound prepared according to the description of paragraph b above, 12 g. of activated $MnO_2$ and 100 ml. of petroleum-ether (30°–40°) were stirred for 15 minutes at room temperature. The solid was removed by filtration and the liquid was dried over molecular sieves then it was concentrated and distilled under reduced pressure. 1.02 g. (81 %) of 2,6,6-trimethyl-1-tetrolyl-1-cyclohexene were thus obtained, the analytical measurements thereof gave the following results: $n_D^{20} = 1.5107$; $d_4^{20} = 0.957$. IR spectrum (liquid phase): 2210 ($\nu_{C \equiv C}$), 1640 ($\nu_{C=O}$) cm$^{-1}$. NMR spectrum ($CCl_4$): 1.08 (3 H, s), 1.68 (3 H, s), 2.02 (3H, s) ppm (δ). Mass spectrum: 190 (28), 175 (100), 67 (63), 123 (37), 41 (25), 81 (24), 135 (22), 28 (21), 91 (20), 147 (20).

EXAMPLE 19

Trans-2,6,6-trimethyl-1-crotonoyl-1-cyclohexene

Under an atmosphere of nitrogen, a solution containing 1.16 g. of cis-2,6,6-trimethyl-1-crotonoyl-1-cyclohexene prepared according to Example 18, 12 ml. of dry benzene and 0.023 g. of p-toluensulfonic acid were stirred 48 hours at room temperature. The solution was diluted with ether, neutralised and washed as usual. The volatile components were removed in vacuo and distillation gave a 90 % yield of trans-2,6,6-trimethyl-1-crotonoyl-1-cyclohexene, b.p. 78°–80°/0.001 Torr, the constants of which were found identical with those of the compound described in Example 12.

EXAMPLE 20

Cis-2,6,6-trimethyl-1-crotonoyl-2-cyclohexene a. 2,6,6-Trimethyl-1-tetrolyl-2-cyclohexene obtained according to the description of paragraph c) hereebelow was hydrogenated according to the method described in Example 18, paragraph a). Thus, cis-2,6,6-trimethyl-1-crotonoyl-2-cyclohexene was obtained in 85–90 % yield. The spectral characteristics were as follows: NMR spectrum ($CCl_4$): 0.85 (3 H, s), 0.96 (3 H, s), 1.62 (3 H, s broad), 2.12 (3 H, d, J = 5.5 cps), 1.0 – 2.3 (4 H, complex band), 2.95 (1 H, s broad), 5.49 (1 H, s broad), 6.25 (2 H, complex band) ppm (δ).

The acetylenic ketone used as starting material in the above preparation can be prepared as follows:

b. 2,6,6-Trimethyl-1-[1-hydroxy-2-butynyl]-2-cyclohexene

Following the procedure described in Example 18 3 g. of α-cyclocitral were reacted with propyne to give 2.0 g. (79 %) of 2,6,6-trimethyl-1-[1-hydroxy-2-butynyl]-2-cyclohexene, b.p. 85°–87°/0.8 Torr. IR spectrum (liquid phase): 3460 ($\nu_{OH}$), 2200 ($\nu_{C \equiv C}$), 1660 ($\nu_{C=C}$) cm$^{-1}$. NMR spectrum ($CDCl_3$): 0.88 (3 H, s), 1.05 (3 H, s), 1.84 (3 H, m), 1.97 (3 H, s), 5.76 (1 H, m) ppm (δ).

c. Oxidation of 2,6,6-trimethyl-1-[1-hydroxy-2-butynyl]-2-cyclohexene

The acetylenic carbinol which was obtained as described above under paragraph b) was oxidised as described for its isomer in Example 18, paragraph c. Thus, 1.38 g. of carbinol gave 0.9 g. (66 %) of 2,6,6-trimethyl-1-tetrolyl-2-cyclohexene, b.p. 100°–105°/0.7 Torr. NMR spectrum ($CCl_4$): 0.96 (6 H, d badly resolved), 1.52 (3 H, m), 2.0 (3 H, s), 5.57 (1 H, m), 2.66 (1 H, m) ppm (δ).

EXAMPLE 21

2,6,6-Trimethyl-1-crotonoyl-2-cyclohexene

Under an atmosphere of nitrogen, 0.5 Mole of lithium α-cyclogeraniate and 6.9 g. (1 Mole) of lithium cut into small pieces were suspended in 1 liter of ether. At room temperature a solution of 0.5 Mole of 1-bromopropene in 250 ml. of ether was added dropwise. Stirring was continued for 24 hours then the whole mixture was poured into an excess of an ice-cold saturated solution of $NH_4Cl$ and stirred vigorously. The organic layer was separated and treated as usual. Distillation of the residue resulting from the removal of the volatile components gave a 36 % yield of 2,6,6-trimethyl-1-crotonoyl-2-cyclohexene.

EXAMPLE 22

Trans-2,6,6-trimethyl-1-crotonoyl-2-cyclohexene a. A mixture of 10 g. of 6,10-dimethyl-4-oxo-2,5,9-undecatrien prepared according to the method of paragraph c hereebelow, 100 ml. of benzene and 1 g. of boron trifluoride etherate was heated to the reflux until the vapour phase chromatographic analysis of a sample showed that practically all the starting material had disappeared. The solution was cooled and stirred with ice-water. The organic layer was removed and treated as usual. Distillation of the residue of evaporation gave a 50 % yield of trans-2,6,6-trimethyl-1-crotonoyl-2-cyclohexene of about 60 % purity as shown by the vapour phase chromatographic analysis.

The ketone used as starting material in the above preparation can be prepared as follows:

b. 6,10-Dimethyl-4-hydroxy-2,5,9-undecatriene 12 g. of magnesium turnings were suspended under nitrogen in 250 ml. of dry tetrahydrofuran. Between 60° and 65°, 60 g. of 1-bromopropene dissolved in 50 ml. of tetrahydrofuran were added dropwise. During the addition, to prevent escaping of 1-bromopropene, the reflux condenser fitted on the reaction flask was cooled to −40°/−50°. When all Mg had reacted, the mixture was cooled to 20° and 76 g. of citral was added dropwise with cooling. After standing overnight, the mixture was poured into 1.5 liter of concentrated aqueous $NH_4Cl$ at 0°. The mixture was extracted 3 times with ether and the combined ether extracts treated as usual. After distillation, 6,10-dimethyl-4-hydroxy-2,5,9-undecatriene, b.p. 70°/0.1 Torr was obtained as a liquid with following constants: $n_D^{20}$ = 1.4950; $d_4^{20}$ = 0.9145.

c. 6,10-Dimethyl-4-oxo-2,5,9-undecatriene 60 g. of the alcohol prepared according to paragraph b above, 700 g. of $MnO_2$ and 1800 ml. of $CH_2Cl_2$ were stirred for 2 days at 20°–25°. After filtration and evaporation, the distillation of the residue gave 49 g. of crude ketone, b.p. 70°–75°/0.1 Torr, which was purified by vapour phase chromatography using a 20 M Carbowax column and helium carrier at 140°. $n_D^{20}$ = 1.5041; $d_4^{20}$ = 0.8958.

EXAMPLE 23

Cis-2,6,6-trimethyl-1-crotonoyl-1,3-cyclohexadiene

Safranal, prepared according to Compt. rend. 262, 1725 (1966), was reacted with propyne to give 2,6,6-trimethyl-1-[1-hydroxy-2-butynyl]-1,3-cyclohexadiene, following the procedure outlined in Example 18, paragraph b, for the reaction of citral with propyne. The above carbinol was oxidised with $MnO_2$ to 2,6,6-trimethyl-1-tetrolyl-1,3-cyclohexadiene, following the procedure described in Example 18, paragraph c), for the oxidation of the dihydro analogue. The above acetylenic ketone was then partially reduced to the title compound following the method described in Example 18, paragraph a). Cis-2,6,6-trimethyl-1-crotonoyl-1,3-cyclohexadiene gave the following NMR data ($CCl_4$): 1.06 (6 H, s), 1.69 (3 H, s), 2.09 (2 H, d, J = 2.3 cps), 2.14 (3 H, d, J = 5.5 cps), 5.81 (2 H, t + s, J = 2.3 cps), 6.2 (2 H, complex band) ppm ($\delta$).

EXAMPLE 24

2,6,6-Trimethyl-1-[2-pentencyl]-2-cyclohexene a. 7,11-Dimethyl-5-oxo-3,6,10-dodecatriene (75 g.), containing a small amount of 7,11-dimethyl-5-oxo-3,6,10-dodecatriene and 11-methyl-7-methylene-5-oxo-3,10-dodecadiene, was added dropwise at 0°–5° under nitrogen to a vigorously stirred solution of tin chloride (30 g.) in 350 ml. of dry benzene.

The reaction mixture kept at 30°–35° was stirred until the analysis by vapour phase chromatography revealed complete disappearance of starting trienes (2–3 h.). It was then poured into crushed ice, extracted with ether and the extracts were combined and washed with water until they were neutral to litmus. After drying, the volatile portions were evaporated and the residue (72 g.) distilled. 22.6 g. (30 % yield) of trans-2,6,6-trimethyl-1-[2-pentenoyl]-2-cyclohexene, B.p. 75°–7°/0.1 Torr, were thus obtained. $n_D^{20}$ = 1.4925; $d_4^{20}$ = 0.9281.

7,11-Dimethyl-5-oxo-3,6,10-dodecatriene used as starting material was prepared as follows:

b. Dehydrolinalool (456 g.; 3 Mole) was added at 20° to a freshly prepared solution of KOH (220 g.; 3.9 Mole), $K_2CO_3$ (30 g.) and $Cu_2Cl_2$ (20 g.) in 1500 ml. of methanol. To this solution 3-chloro-1-butene (352 g.; 3.9 Mole) was then added dropwise with vigorous stirring while the temperature was kept below 50°. Stirring was continued for 3 h. and the residue obtained by evaporating the methanol under reduced pressure was thoroughly mixed with 1 l. of water. This mixture was extracted with ether and after the usual treatments gave by distillation, together with 44 g. of dehydrolinalool, 530 g. of a 85:15 mixture of 7,11-dimethyl-2,10-dodecadiene-5-yn-7-ol (A) and 3,6,10-trimethyl-1,9-undecadiene-4-yn-6-ol (B). These two alcohols were separated by distillation using a spinning band column, and showed the following analytical constants: Compound A (400 g.): B.p. 84°–5°/0.1 Torr; $n_D^{20}$ = 1.4824; $d_4^{20}$ = 0.8872. IR spectrum: 3380, 2235 and 960 $cm^{-1}$. Compound B (80 g.): B.p. 80°/0.1 Torr: $n_D^{20}$ = 1.4789; $d_4^{20}$ = 0.8944. IR spectrum: 3380, 2235, 1640 and 915 $cm^{-1}$.

c. 400 g. of compound A prepared according to paragraph b) were heated during 3 h. at 130° in the presence of 700 g. of acetic anhydride and 60 g. of sodium acetate. The excess of anhydride was then distilled off at 50° under reduced pressure and the residue was treated with water.

This mixture was extracted with petrol-ether, washed with a solution of sodium carbonate and after the usual treatments gave by distillation 414 g. (90 % yield) of the acetate of alcohol A which showed the following analytical constants: B.p. 88°–90°10.1 Torr; $n_D^{20}$ = 1.4732; $d_4^{20}$ = 0.9122. IR spectrum: 2240, 1740 and 965 $cm^{-1}$.

d. 248 g. of the acetate prepared according to paragraph c were heated at 90° during 5 h. in the presence of 500 ml. of acetic acid and 10 g. of copper acetate. By means of vapour phase chromatography it was shown that the starting acetate had completely reacted. The mixture was concentrated in vacuum and the residue was treated with 300 ml. of water. After extraction with petrol-ether and the usual treatments, 190 g. of a mixture consisting of 7,11-dimethyl-5-oxo-3,6,10-dodecatriene and two isomeric ketones, 7,11-dimethyl-5-oxo-3,7,10-dodecatriene and 11-methyl-7-methylene-5-oxo-3,10-dodecadiene, were obtained.

Such a mixture, used directly for the cyclisation process described in paragraph a), had the following analytical constants: B.p. 88°–97°/0.1 Torr; $n_D^{20}$ = 1.4932; $d_4^{20}$ = 0.8919.

EXAMPLE 25

2,6,6-Trimethyl-1-[2-methylcrotonoyl]-2-cyclohexene a. 3,6,10-trimethyl-4-oxo-2,5,9-undecatriene (25 g.), containing a small amount of isomeric ketones 3,6,10-trimethyl-4-oxo-2,6,9-undecatriene and 3,10-dimethyl-6-methylene-4-oxo-2,9-undecadiene, was subjected to cyclisation according to the same procedure described in paragraph a of Example 24, in the presence of 50 ml. of dry benzene and 10 g. of $SnCl_4$. By distillation of 22 g. of crude product, 12.8 g. of an oily substance were obtained. A purification by means of vapour phase chromatography gave 8.8 g. of 2,6,6-trimethyl-1-[2-methylcrotonoyl]-2-cyclohexene, the analytical constants of which are: B.p. 70°–1°/0.1 Torr; $n_D^{20}$ = 1.4818; $d_4^{20}$ = 0.9249. IR spectrum: 1720, 1630, 825, 810 cm$^{-1}$.

The mixture of the ketones used as starting materials in the above preparation was obtained as follows: b. The alcohol B (50 g.), obtained according to the procedure described in paragraph b) of Example 24 was acetylated by means of acetic anhydride (84 g.) in the presence of sodium acetate (8 g.) as described in paragraph c) of Example 24. 54 g. (90 % yield) of the acetate of 3,6,10-trimethyl-1,9-undecadiene-4-yn-6-yl were thus obtained. IR spectrum: 2245, 1745, 1640 and 915 cm$^{-1}$.

c. 37 g. of the acetate prepared according to the method described above were heated at 90° during 5 h. in the presence of 75 ml. of acetic acid and 1.5 g. of copper acetate.

26 g. (85 % yield) of 3,6,10-trimethyl-4-oxo-2,5,9-undecatriene together with two other isomeric ketones, were thus obtained. This mixture was directly used for the cyclisation reaction according to paragraph a.

The mixture had the following analytical constants: B.p. 75°–7°/0.1 Torr; $n_D^{20}$ = 1.4889; $d_4^{20}$ = 0.8890.

EXAMPLE 26

2,6,6-Trimethyl-1-[3-methylcrotonoyl]-2-cyclohexene a. 2,6,10-trimethyl-4-oxo-2,5,9-undecatriene (20 g.) was cyclised according to the procedure described in paragraph a of Example 24 in the presence of 7 g. of SnCl$_4$ in 100 ml. of dry benzene. During the addition of the ketone, the temperature was kept below 150° then it was decreased at 40° while the stirring was continued for 4 hours. According to the usual procedure, 6.8 g. (34 % yield) of pure product were obtained.

B.p. 67°–8°/0.1 Torr; $n_D^{20}$ = 1.4818; $d_4^{20}$ = 0.9249. IR spectrum: 1670, 1615, 826 and 805 cm$^{-1}$.

The starting material accompanied by the isomeric ketones 2,6,10-trimethyl-4-oxo-2,6,9-undecatriene and 2,10-dimethyl-6-methylene-4-oxo-2,9-undecadiene was obtained according to:

b. Methallyl chloride (100 g.) was added portionwise under nitrogen to a solution of KOH (60 g.), K$_2$CO$_3$ (10 g.) and Cu$_2$Cl$_2$ (7 g.) in 500 ml. of methanol. During the addition, the temperature was kept at ca. 40°. The stirring was maintained for 3 more hours then, after evaporation of the volatile components, the residue was treated with 500 ml. of water and 300 ml. of petrol-ether. The extracts were purified and treated according to paragraph b of Example 24.

152 g. (90 % yield) of 2,6,10-trimethyl-2,10-undecadiene-7-yn-6-ol together with 35 g. of dehydrolinalool were obtained. B.p. 70°–2°/0.1 Torr; $n_D^{20}$ = 1.4818, $d_4^{20}$ = 0.8941. IR spectrum: 3350, 2245, 1650 and 890 cm$^{-1}$.

c. 103 g. of the alcohol prepared according to paragraph b) were acetylated with 200 g. of acetic anhydride and 20 g. of sodium acetate according to the procedure described in paragraph c of Example 24. 112 g. (90 % yield) of the corresponding acetate were thus obtained. B.p. 80°/0.01 Torr; $n_D^{20}$ = 1.4709; $d_4^{20}$ = 0.9173. IR spectrum: 2245, 1740, 1645, 890 cm$^{-1}$.

d. 248 g. of the acetate prepared according to paragraph c) were isomerised by acetic acid (400 ml.) and copper acetate (15 g.). 187 g. of a mixture containing 2,6,10-trimethyl-4-oxo-2,5,9-undecatriene and two other isomeric ketones were obtained according to the same procedure described in paragraph d of Example 24.

B.p. 90°–7°/0.1 Torr; $n_D^{20}$ = 1.5075; $d_4^{20}$ = 0.8915.

EXAMPLE 27

Trans-2,6,6-trimethyl-1-crotonoyl-1,3-cyclohexadiene

A mixture of cis- and trans-2,6,6-trimethyl-1-crotonoyl-1,2-epoxycyclohexane (10 g.) obtained according to Example 28 and 2 g. of acid diatomaceous earth in 50 ml. of dioxan was kept under nitrogen at 100°–105° until complete transformation of the starting epoxides into 2,6,6-trimethyl-1-crotonoyl-1,3-cyclohexadiene. The course of the reaction was followed by sample analysis at set time intervals, by means of vapour phase chromatography. After filtration the filtrate was distilled to give 8.0 g. of product B.p. 60°–85°/0.5 Torr, the spectrometric analysis of which revealed a content of 7.5 g. (82 %) of 2,6,6-trimethyl-1-crotonoyl-1,3-cyclohexadiene.

IR: 1670, 1635,1610, 970 cm$^{-1}$. NMR: 1.01 (6 H, s); 1.62 (3 H, s); 1.93 (3 H, d.d., J = 6.5 and 1.5 cps); 2.07 (2 H, d, J = 2.3 cps); 5.77 (2 H, t, J = 2.3 cps); 6.06 (1 H, d.q., J = 16 and 1.5 cps); 6.75 (1 H, d.q. J = 16 and 6.5 cps) δppm. MS: m/e 69–121,105, 41, 190.

The reaction above proceeds through the formation of an hydroxy intermediate, 2,6,6-trimethyl-1-hydroxy-1-crotonoyl-2-cyclohexene, which was isolated by v.p.c. and showed the following analytical data:

IR: 3090, 1675, 1620, 970 cm$^{-1}$. NMR: 0.72 (3 H, s); 0.97 (3 H, s); 1.45 (3 H, m); 1.92 (d, J = 7.5 cps), 4.07 (1 H, m); 5.7 (1 H, m); 6.35–7.2 (2 H, m) δ ppm. MS: M$^+$ = 208 (0.1); m/e = 190 (0.1); 175 (0.1); 165 (0.1); 152 (0.1); 139 (49); 121 (3); 109 (2); 95 (33); 82 (3); 69 (28); 55 (7); 43 (100); 27 (5).

EXAMPLE 28

Cis- and trans-2,6,6-trimethyl-1-crotonoyl-1,2-epoxycyclohexane 2,6,6-Trimethyl-1-vinylacetyl-1,2-epoxycyclohexane (10 g., 95 % pure) and 1 g. of sodium acetate in 50 ml. of dioxan were heated at 100° until complete transformation of the starting epoxyde into 2,6,6-trimethyl-1-crotonoyl-1,2-epoxycyclohexane, the course of the reaction being followed by v.p.c. (Carbowax or Silicone, 180°, 3 m). Two hours are usually required for such a reaction.

After cooling and filtration, the distillation of the mixture gave 9.8 g. of a mixture of the cis- (90 %) and trans- (10 %) isomers.

V.p.c. enabled the separation of the two isomeric compounds:

trans-2,6,6-trimethyl-1-crotonoyl-1,2-epoxycyclohexane B.p. 80°/0.5 Torr; $n_D^{20}$ = 1.4861; $d_4^{20}$ = 0.9849. C$_{13}$H$_{20}$O$_2$ Calc.ed C 74.96; H 9.68, %; Found: C75.02;H 9.64.IR:1700–1620, 968 cm$^{-1}$. NMR: 1.0 and 1.06 (6 H, 2 s); 1.08 (3 H, s); 1.92 (3 H, d, J = 7cps); 6.1–7.2 (2 H, m) δ ppm. MS: M$^+$ = 208 (0.1); m/e = 193 (0.1); 180 (0.1); 165 (0.1); 151 (5); 139 (12); 125 (14); 111 (64); 95 (5); 82 (12); 69 (100); 55 (80); 41 (62); 29 (8).

Cis-2,6,6-trimethyl-1-crotonoyl-1,2-epoxycyclohexane B.p. 79°/0.5 Torr; $n_D^{20}$ = 1.4803; $d_4^{20}$ = 0.9833. C$_{13}$H$_{20}$O$_2$ Calc.ed C 74.96; H 9.68 %; Found C 75.11; H 9.60. IR: 1680, 1615, 748 cm$^{-1}$. NMR: 1.00 and 1.07 (6 H, 2 s); 1.1 (3 H, s); 2.12 (3 H, d, J = 7 cps);

6.0-6.57 (2 H, m) δ ppm. MS: M$^+$ = 208 (0.1); m/e: 193 (1); 175 (0.1); 165 (0.1); 151 (15); 135 (2); 123 (9); 111 (6); 95 (4); 81 (2); 69 (100); 55 (18); 41 (26); 29 (3).

EXAMPLE 29

2,6,6-Trimethyl-1-vinylacetyl-1,2-epoxycyclohexane

A solution of 2,6,6-trimethyl-1-[1-hydroxy-3-butenyl]-1,2-epoxycyclohexane (178.5 g.), obtained according to Example 30, in 265 ml. of toluene was added dropwise with vigorous stirring to a solution of $Na_2Cr_2O_7$ (620 g.) in 500 ml. of conc. $H_2SO_4$ and 1220 ml. of water at 0°–5°. At the same temperature the mixture was kept during 3 h., extracted with ether to give, after the usual treatments, 114.7 g. (67 %) of crude product which after distillation, b.p. 78°/ 0.4 Torr, gave 100 g. (59 %) of an oil. The v.p.c. analysis showed that this oil had a 95 % content of 2,6,6-trimethyl-1-vinylacetyl-1,2-epoxycyclohexane, $n_D^{20\ D}$ = 1.4721; $d_4^{20}$ = 0.9781.

$C_{13}H_{20}O_2$ Calc.ed C 74.96; H 9.68 %; Found C 74.66; H 9.72. IR: 3080, 1820, 1700, 1640, 915, 910 cm$^{-1}$. NMR: 1.02 and 1.05 (6 H, 2 s); 1.1 (3 H, s); 3.2 (2 H, m); 4.8–6.2 (3 H) δ ppm. MS: M$^+$ = 208 (0.1); m/e: 193 (1); 177 (1); 165 (0.1); 151 (15); 135 (2); 123 (8); 111 (4); 95 (3); 81 (2); 69 (100); 55 (18); 41 (29).

EXAMPLE 30

2,6,6-Trimethyl-1-[1-hydroxy-3-butenyl]-1,2-epoxycyclohexane

A mixture of 40 % peracetic acid (105 g.) and anhydrous sodium acetate (3.0 g.) was added at 25° with stirring to a suspension of 2,6,6-trimethyl-1-[1-hydroxy-3-butenyl]-1-cyclohexene (97 g.) and anhyd. sodium acetate (60 g.) in 175 ml. of $CH_2Cl_2$ (1.5 h.). Stirring was continued for one night and 500 ml. of water were then added to the reaction mixture. The organic layer was separated and, after the usual treatments, distilled to give 98 g. (83 %) of two diastereoisomers of the epoxy product.

V.p.c. enabled the separation of the two isomers (Carbowax, 170°, 3 m)

Peak 1: (80 %), b.p. 88-9°/0.5 Torr; $n_D^{20}$ = 1.4790; $d_4^{20}$ = 0.9772 IR: 3540, 1820, 1640, 990, 900 cm$^{-1}$ NMR: 1.0 and 1.03 (6 H, 2 s); 1.42 (3 H, s); 2.52 (1 H, m); 3.92 (1 H, t); 4.7–6.4 (3 H) δ ppm. MS: M$^+$ = 210 (0.1); m/e: 192 (0.1); 177 (0.1); 169 (2); 149 (5); 140 (3); 125 (22); 109 (28); 95 (12); 83 (23); 69 (46); 55 (36); 43 (100); 27 (12).

Peak 2: (20 %), b.p. 93-4°/0.5 Torr; $n_D^{20}$ = 1.4839; $d_4^{20}$ = 0.9945. IR: 3095, 3060, 1635, 990, 910 cm$^{-1}$. NMR: 1.00 and 1.16 (6 H, 2 s); 1.33 (3 H, s); 3.92 (1 H, m); 4.68-6.2 (3 H) δ ppm. MS: M$^+$ = 210 (0.1); m/e: 192 (0.1); 177 (0.1); 169 (2); 149 (5); 140 (2); 119 (59); 109 (34); 95 (13); 83 (25); 69 (47); 55 (42); 43 (100); 27 (13).

2,6,6-Trimethyl-1-[1-hydroxy-3-butenyl]-1-cyclohexene used as starting material in the above preparation, can be obtained as follows:

2,6,6-Trimethyl-1-[1-hydroxy-3-butenyl]-1-cyclohexene 5 g. of allyl chloride were added under nitrogen to a suspension of magnesium (28.8 g.) in 50 ml. dry ether. According to the procedure commonly used for carryinng out a Grignard reaction, allyl chloride (85 g.) and β-cyclocitral (152 g.) in 350 ml. of dry ether were added at such a rate as to maintain the solvent at constant reflux.

At this temperature the mixture was stirred for 3 more hours and poured then into an $NH_4Cl$ aqueous solution.

The ethereal extracts gave by distillation, 178.1 g. (90 %) of the hydroxy-compound (97 % pure). B.p. 50°/0.01 Torr, $n_D^{20}$ = 1.4958; $d_4^{20}$ 32 0.9390.

EXAMPLE 31

Trans-2,6,6-trimethyl-1-[1-hydroxy-2-butenyl]-1,2-epoxycyclohexane 21 g. of 40 % peracetic acid and 0.6 g. of sodium acetate were added under nitrogen to a suspension of 2,6,6-trimethyl-1-[1-hydroxy-2-butenyl]-1-cyclohexene (19.4 g.) and 12 g. of sodium acetate in 35 ml. of $CH_2Cl_2$ at 20°. The reaction mixture was left 2 more hours with stirring and it was then poured into 250 ml. of water.

The organic layer gave by distillation 19.5 g. (93 %) of epoxy product.

B.p. 84°/0.1 Torr; $n_D^{20}$ = 1.4814; $d_4^{20}$ = 0.9933. $C_{13}H_{22}O_2$ Calc.ed C 74.24; H 10.54 %; Found C 73.67; H 10.40. IR: 3090, 960 cm$^{-1}$. NMR: 1.02 (6 H, s); 2.74 (1 H, m); 4.38 (1 H, m); 5.55 (2 H, m) δ ppm. MS: M$^+$ = 210 (0.1); m/e: 192 (0.1); 177 (0.1); 168 (1); 149 (10); 140 (39); 125 (93); 109 (16); 95 (14); 84 (24); 69 (49); 55 (50); 43 (10); 29 (14).

EXAMPLE 32

Trans-2,6,6-trimethyl-1-crotonoyl-1,2-epoxycyclohexane

A solution of trans-2,6,6-trimethyl-1-[1-hydroxy-2-butenyl]-1,2-epoxycyclohexane in 20 ml. of toluene was added at 0–5° with vigorous stirring to a solution of $Na_2Cr_2O_7$ (31 g.) in 25 g. of conc. $H_2SO_4$ and 60 ml. of water. The mixture was kept at 0°–5° during 3 h., then at room temperature during one night. After addition of 250 ml. of water, the mixture was extracted with 100 ml. of pet.-ether and the extracts evaporated. Distillation of the obtained residue gave a colourless oil (5.2 g.) and 6.1 g. of residue.

The v.p.c. analysis showed that the oil had a 4.5 g. (35%) content of trans-2,6,6-trimethyl-1-crotonoyl-1,2-epoxycyclohexane.

EXAMPLE 33

Trans-2,6,6-trimethyl-1-crotonoyl-1,2-epoxycyclohexane

Trans-2,6,6-trimethyl-1-[1-hydroxy-2-butenyl]-1,2-epoxycyclohexane (2.1 g.) and 20 g. of $MnO_2$ (freshly activated by heating it at 100°–105° during 1 h.) in 50 ml. of pet.-ether were mixed and allowed to react at room temperature. The course of the reaction was followed by v.p.c analysis of sample aliquots. After ca. 12 h., 70 % of the starting alcohol was oxidised into the corresponding ketone.

After filtration, a novel portion of $MnO_2$ (10 g.) was added and the same operation was started again until obtainment of 90 % of the desired ketone. By distillation 1.9 g. of product were obtained:

1.2 g. (60 %) of trans-2,6,6-trimethyl-1-crotonoyl-1,2-epoxycyclohexane 0.15 g . (8 %) of starting material 0.55 g. of by-products.

EXAMPLE 34

2,6,6-Trimethyl-1-[1-hydroxy-3-butenyl]-2-cyclohexene

Allyl chloride (5 ml.) was added under nitrogen to a suspension of magensium (28.8 g.) in 300 ml. of dry ether. According to the usual procedure of a Grignard reaction, allyl chloride (85 g.) and α-cyclocitral (152 g.) in 100 ml. of dry ether were added at such a rate as to maintain the solvent at reflux. At this temperature, the mixture was left during 3 h. and poured then into an NH$_4$Cl aqueous solution.

The ethereal layer gave by evaporation and subsequent distillation 182 g. (95 %) of a mixture of the two diastereoisomers of the hydroxy compound: V.p.c. (Carbowax, 170°, 3 m) enabled the separation of the two isomers:

Peak 1: ca. 70 %; b.p. 62°/0.1 Torr, $n^{20}_D$ = 1.4878; $d^{20}_4$ = 0.9276.

C$_{13}$Hh$_{22}$O Calc.ed C 80.35; H 11.44 %;
Found C 79.87; H 11.26.

IR: 3400, 3060, 1820, 1635, 988, 910 cm$^{-1}$.

NMR: 0.85 and 0.98 (6 H, 2 s); 1.75 (3 H, s); 3.75 (1 H, t); 5.6 (1 H, m); 4.88–6.0 (3 H) δ ppm.

The mass spectrum was practically identical to that of the product corresponding to peak 2.

Peak 2: ca. 30 %; b.p. 62°/0,1 Torr; $n^{20}_D$ = 1.4922; $d^{20}_4$ = 0.9319.

C$_{13}$H$_{22}$O Calc.ed C 80.35; H 11.44 %;
Found C 79.91; H 11.19 %

IR: 3420, 3070, 1815, 1630, 985, 910 cm$^{-1}$.

NMR: 0.91 and 1.05 (6 H, 2 s); 1.78 (3 H, m); 4.82 (m);
5.45 (1 H, m); 4.86–6.2 (3 H) δ ppm.

MS: M$^+$ = 194 (0.1); m/e: 176 (0.1); 161 (0.1); 153 (2); 135 (2); 124 (64); 109 (100); 95 (13); 81 (27.5); 68 (31); 55 (10); 41 (30); 27 (8).

EXAMPLE 35

2,6,6-Trimethyl-1-vinylacetyl-2-cyclohexene

A solution of 2,6,6-trimethyl-1-[1-hydroxy-3-butenyl]-2-cyclohexene (191.4 g.), prepared according to Example 34, in 310 ml. of toluene was added dropwise with vigorous stirring at 0°–5° to a solution of Na$_2$Cr$_2$O$_7$. 2 H$_2$O (365 g.) in 300 g. of conc. H$_2$SO$_4$ and 1800 ml. of water (1.5 h.).

The reaction mixture was left at room temperature during 10 h. and, after separation of the organic phase, 300 ml. of pet.-ether were added to it.

The combined organic extracts gave after the usual treatments and distillation 170 g. of a product b.p. 50°–3°/0.1 Torr, which had a 90 % content of 2,6,6-trimethyl-1-vinylacetyl-2-cyclohexene. Yield ca. 80 %.

As sample purified by v.p.c. showed the following analytical data:

B.p. 53°/0.1 Torr; $n^{20}_D$ = 1.4830; $d^{20}_4$ = 0.9371.

C$_{13}$H$_{20}$O Calc.ed C 81.20; H 10.48 %;
Found C 80.21; H 10.43.

IR: 3080, 1820, 1710, 1640, 990, 900, 808 cm$^{-1}$.

NMR: 0.88 and 0.93 (6 H, 2 s); 1,58 (3 H, s); 3.17 and 3.27 (2 H, 2 m); 5.55 (1 H, m); 4.85–6.3 (3 H) δ ppm.

MS: M$^+$ = 192 (5); m/e: 177 (0.1); 166 (0.1); 151 (12); 135 (1); 123 (100); 107 (6); 95 (10); 81 (80); 69 (60); 55 (10); 41 (44); 27 (5).

EXAMPLE 36

Trans-2,6,6-trimethyl-1-crotonoyl-2-cyclohexene 2,6,6-Trimethyl-1-vinylacetyl-2-cyclohexene (170 g.), obtained according to Example 35, was heated during 1 h. with ca. 1 ml. of conc. HCl in 500 ml. of tetrahydrofuran. The solution was concentrated in vacuo to a volume of ca. 300 ml., then 300 ml. of pet.-ether and 300 ml. of a diluted NaHCO$_3$ solution were added to it.

The organic phase gave, after the usual treatments, 168 g. of a product, b.p. 52°–55°/0.1 Torr, which had a 92 % content of trans-2,6,6-trimethyl-1-crotonoyl-2-cyclohexene.

NMR: 0.85 and 0.96 (6 H, 2 s); 1.62 (3 H, s); 2.12 (3 H, d, J = 5.5 cps); 1.0–2.3 (4 H, complex band); 2.95 (1 H, s); 5.49 (1 H, s); 6.25 (2 H, complex band) δ ppm.

EXAMPLE 37

2,6,6-Trimethyl-1-hydroxy-1-crotonoyl-2-cyclohexene

A mixture of the cis- and trans-isomers of 2,6,6-trimethyl-1-crotonoyl-1,2-epoxycyclohexane (10 g.) [cf. Example 32 ] and 2 g. of acid diatomaceous earth in 50 ml. of dioxan was heated under nitrogen at 100°–105°.

The course of the reaction was followed by v.p.c. analysis of sample aliquots taken at set time intervals. After filtration and purification, the product had the following analytical data:

$n^{20}_D$ = 1.5049; $d^{20}_4$ = 1.018

C$_{13}$H$_{20}$O$_2$ Calc.ed C 74.96; H 9.68 %;
Found C 74.68; H 9.69 %.

IR: 3090, 1675, 1620, 970 cm$^{-1}$.

NMR: 0.72 and 0.97 (6 H, 2 s); 1.45 (3 H, m); 1.92 (d, J = 7.5 cps), 4.07 (1 H, m); 5.7 (1 H, m); 6.35–7.2 (2 H, m) δ ppm.

MS: M$^+$ = 208 (0.1), m/e: 190 (0.1); 175 (0.1); 165 (0.1); 152 (0.1); 139 (49); 121 (3); 109 (2); 95 (33); 82 (3); 69 (28); 55 (7); 43 (100); 27 (5).

EXAMPLE 38

Aromatization of corn-syrup

A base composition of corn-syrup was aromatized by the addition of 2,6,6-trimethyl-1-hydroxy-1-crotonoyl-2-cyclohexene, as unique ingredient, in the proportion of 0.03 g. of a 1 % solution in 95 % alcohol for 100 ml. of base syrup.

The syrup thus obtained, contrary to the base syrup which had a bland taste, possesses a taste of honey and a light flavour note which reminds of roasted hazelnuts.

EXAMPLE 39

Aromatization of black-tea

A test solution of black tea was obtained by brewing during 5 minutes 6 g. of bland taste black-tea leaves of commercial quality in 600 ml. of boiling water. When to 100 ml. of this solution 0.05 g. of a 1 % solution of 2,6,6-trimethyl-1-crotonoyl-2,3-epoxycyclohexane in 95 % alcohol were added, a solution with a more herb-like note which distinctly reminded of camomile was obtained.

EXAMPLE 40

Perfume composition of Chypre type

A perfume composition of Chypre type was obtained by admixing the following ingredients (parts by weight):

| | |
|---|---|
| Bergamot | 21 |
| Portugal | 0.5 |
| Synthetic Neroli | 1 |
| Synthetic rose | 9 |
| Synthetic Jasmine | 9 |
| Ylang extra | 6 |
| Methylionone | 6 |
| Hydroxycitronellal | 6 |
| Oriental santal | 3 |
| Patchouli | 1.5 |
| Vetyveryl acetate | 4.5 |
| Natural degreased civet 10 % sol. * | 3 |
| Ciste labdanum absolute 10 % sol. * | 2 |
| Musk ketone | 4 |
| 1,1-Dimethyl-6-tert.butyl-4-acetyl-indane | 0.5 |
| Coumarin | 3 |
| Trichloromethylphenylcarbinyl acetate | 1.5 |
| Tarragon 10 % sol. * | 3 |
| Oak moss absolute 50 % sol. * | 6 |
| Benjoin resin 10 % sol. * | 1.5 |
| Styrax cinnamic alcohol | 1.5 |
| Jasmine absolute | 1.5 |
| Rose absolute | 1 |
| Cyclopentadecanolide 10 % sol. * | 2 |
| Methylnonylacetic aldehyde | 1.5 |

*in diethylphthalate

By adding to 99.5 g. of this mixture 0.5 g. (as a 10 % solution in diethylphthalate) of cis- or trans-2,6,6-trimethyl-1-crotonoyl-1,2-epoxycyclohexane the composition obtained was more powerful than the basic composition and had improved diffusion as well as very natural richness.

EXAMPLE 41

Perfume composition of the chypre type

A chypre type composition was prepared by mixing the following ingredients (parts by weight):

| | |
|---|---|
| Bergamot | 21 |
| Portugal | 0.5 |
| Synthetic Neroli | 1 |
| Synthetic Rose | 9 |
| Synthetic Jasmine | 9 |
| Ylang extra | 6 |
| Methylionone | 6 |
| Hydroxycitronellal | 6 |
| Oriental santal | 3 |
| Patchouli | 1.5 |
| Vetyveryl acetate | 4.5 |
| Natural degreased civet 10 % sol. * | 3 |
| Ciste labdanum absolute 10 % sol. * | 2 |
| Musk ketone | 4 |
| 1,1-Dimethyl-6-tert.butyl-4 acetyl indane | 0.5 |
| Coumarin | 3 |
| Trichloromethylphenylcarbinyl acetate | 1.5 |
| Tarragon 10 % sol. * | 3 |
| Oak moss absolute 50 % sol. * | 6 |
| Benjoin resin 10 % sol. * | 1.5 |
| Styrax cinnamic alcohol | 1.5 |
| Jasmine absolute | 1.5 |
| Rose absolute | 1 |
| Cyclopentadecanolide 10 % sol. | 2 |
| Methylnonylacetic aldehyde | 1.5 |

*in diethyl phthalate

By adding to 99.5 g. of this mixture 0.5 g. ** of trans- or cis-2,6,6-trimethyl-1-crotonoyl-1-cyclohexene the composition obtained was more powerful than the basic composition and had an improved diffusion as well as a very natural richness.
(** as a 10 % solution in diethyl phthalate)

EXAMPLE 42

Perfume composition of the floral type

A floral type composition was prepared by mixing the following ingredients (parts by weight):

| | |
|---|---|
| Decanal 10 % sol. * | 1 |
| Undecanal 10 % sol. * | 2 |
| Lauric aldehyde 10 % sol. * | 1 |
| Methylnonylacetic aldehyde 10 % sol. * | 0.5 |
| Synthetic lily-of-the-valley | 16.5 |
| Synthetic lilac | 3 |
| Synthetic rose | 7 |
| Synthetic jasmine | 12 |
| Bergamot | 6 |
| Tarragon 10 % sol. * | 3 |
| Ylang extra | 9 |
| Synthetic carnation | 6 |
| Methylionone | 6 |
| Vetiveryl acetate | 4 |
| Santalol | 2 |
| Decoloured oak moss absolute 10 % sol. * | 3 |
| Natural degreased civet 10 % sol. * | 3 |
| Lily absolute 1 % sol. * | 2 |
| Orange blossom absolute 10 % sol. * | 2 |
| Jasmine absolute | 2 |
| Rose absolute | 1 |
| Musk ketone | 4 |
| Trichloromethylphenylcarbinyl acetate | 2 |
| Colourless Tolu resin absolute 10 % sol. | 1.5 |

*in diethyl phthalate

By adding to 99.5 g. of this mixture 0.5 g. ** of trans- or cis-2,6,6-trimethyl-1-crotonoyl-1-cyclohexene the composition obtained was more powerful than the basic composition and had an improved diffusion as well as a very natural richness.
** (as a 10 % solution in diethyl phthalate)

EXAMPLE 43

Perfume composition of the floral type

A floral type composition was prepared by mixing the following ingredients (parts by weight):

| | |
|---|---|
| Rhodinol | 24 |
| l-Citronellol | 21 |
| Chemically pure geraniol | 12 |
| Phenylethyl alcohol | 24 |
| Linalool | 2.5 |
| Farnesol | 2 |
| Eugenol | 0.5 |
| Methyleugenol | 2 |
| Neryl isobutyrate | 0.5 |
| Phenylethyl phenylacetate | 0.5 |
| Geranyl acetate | 1 |
| Guaiol acetate | 0.5 |
| Citral 10 % sol. * | 2.5 |
| Nonanol 10 % sol. * | 0.5 |
| Nonanal 10 % sol. * | 0.5 |
| Decanal 1 % sol. * | 2 |
| Undecanal 10 % sol. * | 0.5 |
| Deterpenated geranium oil | 1.5 |
| Phenylethylsalicylate | 0.5 |

*in diethyl phthalate

By adding to 98.5 g. of this mixture 1.5 g. of trans- or cis-2,6,6-trimethyl-1-crotonoyl-1-cyclohexene the composition obtained was more powerful than the basic composition and had an improved diffusion as well as a very natural richness.

EXAMPLE 44

Perfume composition of the floral type

A floral type composition was prepared by mixing the following ingredients (parts by weight):

| | |
|---|---|
| Rhodinol | 24 |
| l-Citronellol | 21 |
| Chemically pure geraniol | 12 |

-continued

| | |
|---|---|
| Phenylethyl alcohol | 24 |
| Linalool | 2.5 |
| Farnesol | 2 |
| Eugenol | 0.5 |
| Methyleugenol | 2 |
| Neryl isobutyrate | 0.5 |
| Phenylethyl phenylacetate | 0.5 |
| Geranyl acetate | 1 |
| Guaiol acetate | 0.5 |
| Citral 10 % sol. * | 2.5 |
| Nonanol 10 % sol. * | 0.5 |
| Nonanal 10 % sol. * | 0.5 |
| Decanal 1 % sol. * | 2 |
| Undecanal 10 % sol. * | 0.5 |
| Deterpenated geranium oil | 1.5 |
| Phenylethyl salicylate | 0.5 |

*in diethyl phthalate

By adding to 98.5 g. of this mixture 1.5 g. of trans-2,6,6-trimethyl-1-crotonoyl-1,3-cyclohexadiene ** the composition obtained was more powerful than the basic composition and had an improved diffusion as well as a very natural richness.

** (as a 10 % solution in diethyl phthalate)

EXAMPLE 45

Perfume composition of the floral type

A floral type composition was prepared by mixing together the following ingredients (parts by weight):

| | |
|---|---|
| Nonanal at 1 % * | 5 |
| Dodecanal at 10 % * | 5 |
| Undecanal at 10 % * | 20 |
| Oil of Coriander | 20 |
| Neroli bigarade | 5 |
| Styrax | 40 |
| l-Citronellol | 50 |
| Phenylethyl alcohol | 100 |
| Phenylacetaldehyde at 10 % * | 10 |
| Eugenol | 30 |
| Ylang | 80 |
| Artificial jasmine | 60 |
| α-Amyl-cinnamaldehyde | 40 |
| Hydroxycitronnellal | 85 |
| Santal oriental | 70 |
| Vetiveryl acetate | 100 |
| Vetiverol | 10 |
| Purified Civet at 10 % * | 30 |
| Musk ambrette | 20 |
| Musk ketone | 30 |
| Coumarin | 50 |
| Pentadecanolide at 10 % * | 20 |
| Bergamot | 100 |
| Total | 980 |

*in diethyl phthalate

By adding to 980 g. of the above mixture 20 g. of trans-2,6,6-trimethyl-1-crotonoyl-1,3-cyclohexadiene**, the composition obtained had an improved floral note, a natural richness, more body and a better diffusion than the base composition.

** (as a 10 % solution in diethyl phthalate)

EXAMPLE 46

Preparation of a "Tutti-Frutti" flavouring composition

A Tutti-Frutti flavouring composition was prepared by mixing together the following ingredients (parts by weight):

| | |
|---|---|
| Vanillin | 20 |
| Allyl caproate | 10 |
| Citral | 20 |
| Amyl butyrate | 35 |
| Orange oil | 45 |
| Ethyl butyrate | 75 |
| Ethyl acetate | 185 |
| Amyl acetate | 185 |
| Lemon oil | 415 |
| Total | 990 |

Trans-2,6,6-trimethyl-1-crotonoyl-1-cyclohexene (10 g.) was added to 990 g. of the above mixture which was then called "test" composition. A "control" composition was prepared by adding 10 g. of additional lemon oil to 990 g. of the above mixture.

The test and control compositions were added to the food products described hereinafter in the proportions shown for 100 kg. of material to be flavoured.

| | |
|---|---|
| Cake | 20 g. |
| Pudding | 5 – 10 g. |
| Cooked sugar | 15 – 20 g. |

Cooked sugar:

100 ml. of sugar syrup (prepared by dissolving 1 kg. of sucrose in 600 ml. of water) and 20 g. of glucose were mixed together and slowly heated to 145°. The flavour was added and the mass was allowed to cool and harden.

Pudding:

to 500 ml. of warmed milk were added with stirring a mixture of 60 g. of sucrose and 3 g. of pectin. The mixture was boiled for a few seconds and the flavour was added. The mixture was allowed to cool.

Cake:

the following ingredients were mixed together: 100 g. of vegetable margarine, 1.5 g. of sodium chloride, 100 g. of sucrose, 2 eggs and 100 g. of flour. The flavour was added and the mass was cooked for 40 minutes at 180°.

The finished foodstuff samples were tested by a panel of trained persons who had to express their views about the flavour of the samples. All members of the panel declared with no hesitation that the "test" samples had a more "round" taste than the "control" and at the same time a red berry character.

When in the above example, 2,6,6-trimethyl-1-crotonoyl-1-cyclohexene was replaced by 2,6,6-trimethyl-1-crotonoyl-1,3-cyclohexadiene, the test samples obtained therefrom were judged to have also a rounder taste than the control with however a more flowery and less fruity character than the test samples containing 2,6,6-trimethyl-1-crotonoyl-1-cyclohexene.

EXAMPLE 47

Preparation of a flavour composition for monastery type liquor

A flavouring composition for monastery type liquors was prepared by mixing together the following ingredients (parts by weight):

| | |
|---|---|
| Oil of Neroli | 5 |
| Oil of Clove | 20 |
| Oil of Cardamone | 25 |
| Oil of nutmeg | 25 |
| Oil of cinnamon | 25 |
| Lemon oil | 35 |
| Oil of sweet orange | 65 |
| Angelica seed oil | 75 |
| Peppermint oil | 75 |
| Oil of bitter orange | 200 |
| Angelica root oil | 445 |
| Total | 995 |

Trans-2,6,6-trimethyl-1-crotonoyl-1-cyclohexene (5 g.) was added to 995 g. of the above mixture which was then called the test composition. A control composition resulted from the addition of 5 g. of Angelica root oil to 995 g. of the above mixture.

A liquor base was prepared by mixing the following ingredients:

| | |
|---|---|
| Alcohol 64 o.p. (96 %) | 325 ml. |
| wine alcohol (74 %) | 100 ml. |
| sugar syrup (65 %) | 10 ml. |
| water | 565 ml. |
| Total | 1000 ml. |

The liquor base was flavoured by adding to 100 kg. thereof 10 g. of the flavouring compositions. The finished liquor samples were tested by a panel of tasters in the same manner as described in Example 46. All members of the panel declared with no hesitation that the test sample had a rounder taste than the control and at the same time a red berry character.

When in the above example, 2,6,6-trimethyl-1-crotonoyl-1-cyclohexene was replaced by 2,6,6-trimethyl-1-crotonoyl-1,3-cyclohexadiene, similar results were experienced. However, the test samples were also judged to have a more flowery and less fruity character than those containing 2,6,6-trimethyl-1-crotonoyl-1-cyclohexene.

EXAMPLE 48

Flavouring of foodstuffs and beverages

Trans-2,6,6-trimethyl-1-crotonoyl-1-cyclohexene was used as sole ingredient to flavour the following edible goods at the doses indicated (parts by weight):
a. Red wine, 0.2 – 1 ppm
b. Raspberry syrup, 0.3 – 0.6 ppm (based on diluted syrup)
c. Honey, 05 – 1 ppm In cases a, b and c the bouquet of the goods was markedly improved. In a) the fruity side was also improved and in c) the flowery note was furthermore enhanced. In b) a cooked fruit note was noticed.

EXAMPLE 49

1,5,5,8,9-Pentamethylbicyclo[4.3.0]non-8-en-7-one

A solution of 2,6,6-trimethyl-1-[2-methylcrotonoyl]-1-cyclohexene (1.0 g.) in 10 ml. of dioxan was heated at 100° under nitrogen with acidic diatomaceous earth (0.2 g.) until complete conversion of the starting material into the bicyclic ketone. The course of the reaction was followed by v.p.c. analysis of sample aliquots taken at set time intervals. Three hours were usually required for such a reaction.

After filtration over diatomaceous earth and evaporation of the clear filtrate, a residue was obtained which, by fractional distillation, gave 1,5,5,8,9-pentamethylbicyclo[4.3.0]non-8-en-7-one in 84 % yield.
$n_D^{20} = 1.5020$; $d_4^{20} = 0.9688$
MS: $M^+ = 206$ (20); IR: 1655 and 1690 cm$^{-1}$.
NMR: 0.82 and 1.18 (6 H, 2 s); 1.18 (3 H, s); 1.91 (3 H, s); 1.54 (3 H, s) δ ppm.

EXAMPLE 50

1,4,5,5,8,9-Hexamethylbicyclo[4.3.0]non-8-en-7-one

According to the same procedure described in Example 49, a solution of 2,4,6,6-tetramethyl-1-[2-methylcrotonoyl]-1-cyclohexene (1.0 g.) in 10 ml. of dioxan was heated at 100° under nitrogen with acidic diatomaceous earth (0.2 g.).

Fractional distillation gave the desired bicyclic ketone in 65 % yield.
$n_D^{20} = 1.5042$; $d_4^{20} = 0.9766$.
IR: 1625 and 1690 cm$^{-1}$.

EXAMPLE 51

1,5,5,9-Tetramethylbicyclo[4.3.0]nona-2,8-dien-7-one

A solution of 2,6,6-trimethyl-1-crotonoyl-1,3-cyclohexadiene (1.0 g.) in 10 ml. of dioxan was heated under the same conditions as described in Example 49 with acidic diatomaceous earth (0.2 g.).

The usual treatment and distillation yielded the desired bicyclic ketone.
Yield ca. 80 %; $n_D^{20} = 1.5080$; $d_4^{20} = 0.9895$.
MS: $M^+ = 190$.
IR: 1620 and 1680 cm$^{-1}$.
NMR: 0.84 and 1.13 (6 H, 2 s); 2.08 (3 H, m); 5.61 (1 H, m); 5.72 (2 H, m) δ ppm.

EXAMPLE 52

4,4,8-Trimethyl-9-methylene-bicyclo[3.3.1]nonan-6-one

A solution of 2,6,6-trimethyl-1-crotonoyl-2-cyclohexene (1.0 g.) in a mixture of benzene and ether (10 ml.) was heated at ca. 80° in the presence of a catalytic amount of a saturated solution of $BF_3$ in ether. The course of the reaction was followed by v.p.c. analysis. Three hours were usually necessary for converting the starting material into the bicyclic compound.

The usual treatment followed by fractional distillation gave the desired ketone in 88 % yield.
$n_D^{20} = 1.4955$; $d_4^{20} = 0.9642$.
MS: $M^+ = 192$ (60); IR: 1650 and 1700 cm$^{-1}$.
NMR: 1.02 (3 H, d, J = 7 cps); 0.84 and 0.99 (6 H, 2 s); 4.58 and 4.78 (2 H, 2 m) δ ppm.

EXAMPLE 53

Preparation of a "Tutti-Frutti" flavouring composition

A Tutti-Frutti flavouring composition was prepared by admixing the following ingredients (parts by weight):

| | |
|---|---|
| Vanillin | 20 |
| Allyl caproate | 10 |
| Citral | 20 |
| Amyl butyrate | 35 |
| Orange oil | 45 |
| Ethyl butyrate | 75 |
| Ethyl acetate | 185 |
| Amyl acetate | 185 |
| Lemon oil | 400 |
| Total | 975 |

1,5,5,9-Tetramethylbicyclo[4.3.0]nona-2,8-dien-7-one (25 g.) was added to 975 g. of the above mixture which was then called test composition. A control composition was prepared by adding 25 g. of additional lemon oil to 975 g. of the above mixture.

The test and control compositions were added to the food products described hereinafter in the proportions shown for 100 kg. of material to be flavoured.

| | |
|---|---|
| Cake | 20 g. |
| Pudding | 5 – 10 g. |
| Cooked sugar | 15 – 20 g. |

Cooked sugar:

100 ml. of sugar syrup (prepared by dissolving 1 kg. of sucrose in 600 ml. of water) and 20 g. of glucose were mixed together and slowly heated to 145°. The flavour was added and the mass was allowed to cool and harden.

Pudding:

to 500 ml. of warmed milk were added with stirring a mixture of 60 g. of sucrose and 3 g. of pectin. The mixture was boiled for a few seconds and the flavour was added. The mixture was allowed to cool.

Cake:

the following ingredients were mixed together: 100 g. of vegetable margarine, 1.5 g. of NaCl, 100 g. of sucrose, 2 eggs and 100 g. of flour. The flavour was added and the mass was cooked for 40 minutes at 180°. The finished foodstuff samples were tested by a panel of trained persons who had to express their views about the flavour of the samples. All members of the panel declared with no hesitation that the test samples had a more distinguished fruity- and woody-note than the control samples and at the same time a red berry character.

EXAMPLE 54

6,6 -Dimethyl-2-methylene-1-crotonoylcyclohexane and 1,5,5,9-tetramethylbicyclo[4.3.0]non-8-en-7-one.

$H_2O_2$ (30 %, 120 ml.) and 6N NaOH (30 ml.) were added to a solution of γ-ionone (50 g.) in 3 l. of MeOH. To the reaction mixture, stirred at room temperature for 24 h., 50 ml. of $H_2O_2$ (30 %) were added and the stirring was continued for 24 h. more. The addition of hydrogen peroxide was repeated and after a total of 3 consecutive days the solution was concentrated in vacuo and the residue distilled.

The fractional distillation yielded 46 g. of a 55:45 mixture of 2 isomeric epoxides of γ-ionone (epoxides A and B) which could be separated by means of a spinning-band-column distillation or v.p.c. (Carbowax 20 M).

Epoxide A, b.p. 88°–9°/0.1 Torr; $n_D^{20}$ = 1.4890;
Epoxide B, b.p. 90°–1°/0.1 Torr; m.p. 43°–4°.

Epoxide A (5 g.) in 5 ml. of MeOH were added dropwise at 0° under nitrogen to a solution of 10 ml. of pure hydrazine hydrate in 5 ml. of MeOH (1.5 h.). After 2 hours stirring, the mixture underwent the usual treatments and gave by distillation (36 % yield): cis-(isomer 8 %) 6,6-dimethyl-1-[1-hydroxy-2-butenyl]-2-methylene cyclohexane, the trans-derivative of the same alcohol (isomer A, 7 %) and 1,5,5,9-tetramethylbicyclo[4.3.0]non-8-en-7-ol (isomer A, 80 %). These compounds have been separated by preparative v.p.c.

In the above procedure, by substituting epoxide A with epoxide B, 6,6,-dimethyl-1[1-hydroxy-2-butenyl]-2-methylencyclohexane, cis-, (isomer B, 36 %) the transderivative of the same alcohol (isomer B, 58 %) and 1,5,5,9-tetramethylbicyclo[4.3.0]non-8-en-7-ol (isomer B, 2 %) were obtained.

The mixture of 6,6-dimethyl-1-[1-hydroxy-2-butenyl]-2-methylencyclohexane, form cis-, isomers A and B, and trans-, isomers A and B, was oxidised by means of chromic anhydride in the presence of pyridine [cf. J. Am. Chem. Soc. 75, 422 (1953)]. A mixture of the cis- and trans-isomers of 6,6-dimethyl-2-methylene-1-crotonoyl cyclohexane were thus obtained in 70 % yield. The two products were separated by preparative v.p.c.

Isomer cis- (more volatile): $n_D^{20}$ = 1.4892; $d_4^{20}$ = 0.9342.

Isomer trans-: $n_D^{20}$ = 1.4939; $d_4^{20}$ = 0.9335

According to the same procedure, a mixture of the two isomers of the bicyclic carbinol was oxidised and yielded 1,5,5,9-tetramethylbicyclo[4.3.0]non-8-en-7-one. $n_D^{20}$ = 1.5028; $d_4^{20}$ = 0.9874.

The mixture of the 6 hydroxylic derivatives obtained by simultaneous isomerization of the 2 epoxides (isomers A and B) could be oxidised according to the same procedure as used for the separated compounds. The oxidised derivatives were obtained in a comparable yield and were separated by means of preparative v.p.c.

EXAMPLE 55

Preparation of a "Tutti-Frutti" flavouring composition

A Tutti-Frutti flavouring composition was prepared by admixing the following ingredients (parts by weight):

| | |
|---|---|
| Vanillin | 20 |
| Allyl caproate | 10 |
| Citral | 20 |
| Amyl butyrate | 35 |
| Orange oil | 45 |
| Ethyl butyrate | 75 |
| Ethyl acetate | 185 |
| Amyl acetate | 185 |
| Lemon oil | 400 |
| Total | 975 |

1,5,5,9-Tetramethylbicyclo[4.3.0]non-8-en-7-one (25 g.) was added to 975 g. of the above mixture which was then called test composition. A control composition was prepared by adding 25 g. of additional lemon oil to 975 g. of the above mixture.

The test and control compositions were added to the food products described hereinafter in the proportions shown for 100 kg. of material to be flavoured.

| | |
|---|---|
| Cake | 20 g. |
| Pudding | 5 – 10 g. |
| Cooked sugar | 15 – 20 g. |

Cooked sugar:

100 ml. of sugar syrup (prepared by dissolving 1 kg. of sucrose in 600 ml. of water) and 20 g. of glucose were mixed together and slowly heated to 145°. The flavour was added and the mass was allowed to cool and harden.

Pudding:

to 500 ml. of warmed milk were added with stirring a mixture of 60 g. of sucrose and 3 g. of pectin. The mixture was boiled for a few seconds and the flavour was added. The mixture was allowed to cool.

Cake:

the following ingredients were mixed together: 100 g. of vegetable margarine, 1.5 g. of NaCl, 100 g. of sucrose, 2 eggs and 100 g. of flour. The flavour was added and the mass was cooked for 40 minutes at 180°.

The finished foodstuff samples were tested by a panel of trained persons who had to express their views about the flavour of the samples. All members of the panel declared with no hesitation that the test samples had a more distinguished fruity- and flowery-note than the control samples and at the same time rounder character.

EXAMPLE 56

Perfume composition of the chypre type

A chypre type composition was prepared by mixing the following ingredients (parts by weight):

| | |
|---|---|
| Bergamot | 21 |
| Portugal | 0.5 |
| Synthetic Neroli | 1 |
| Synthetic Rose | 9 |
| Synthetic Jasmine | 9 |
| Ylang extra | 6 |
| Methylionone | 6 |
| Hydroxycitronellal | 6 |
| Oriental santal | 3 |
| Patchouli | 1.5 |
| Vetiveryl acetate | 4.5 |
| Natural degreased civet 10 % sol. * | 3 |
| Ciste labdanum absolute 10 % sol. * | 2 |
| Musk ketone | 4 |
| 1,1-Dimethyl-6- tert. butyl-4-acetyl-indane | 0.5 |
| Coumarin | 3 |
| Trichloromethylphenylcarbinyl acetate | 1.5 |
| Tarragon 10 % sol. * | 3 |
| Oak moss absolute 50 % sol. * | 6 |
| Benjoin resin 10 % sol. * | 1.5 |
| Styrax cinnamic alcohol | 1.5 |
| Jasmine absolute | 1.5 |
| Rose absolute | 1 |
| Cyclopentadecanolide 10 % sol. | 2 |
| Methylnonylacetic aldehyde | 1.5 |
| *in diethyl phthalate | |

By adding to 99.5 g. of this mixture 0.5 g. ** of trans-2,4,6,6-tetramethyl-1-crotonoyl1-cyclohexene the composition obtained was more powerful than the basic composition and had an improved diffusion as well as a very natural richness.
(** as a 10 % solution in diethyl phthalate)

EXAMPLE 57

Perfume composition of the floral type

A floral type composition was prepared by mixing the following ingredients (parts by weight):

| | |
|---|---|
| Decanol 10 % sol. * | 1 |
| Undecanal 10 % sol. * | 2 |
| Lauric aldehyde 10 % sol. * | 1 |
| Methylnonylacetic aldehyde 10 % sol. * | 0.5 |
| Synthetic lily-of-the-valley | 16.5 |
| Synthetic lilac | 3 |
| Synthetic rose | 7 |
| Synthetic jasmine | 12 |
| Bergamot | 6 |
| Tarragon 10 % sol. * | 3 |
| Ylang extra | 9 |
| Synthetic carnation | 6 |
| Methylionone | 6 |
| Vetiveryl acetate | 4 |
| Santalol | 2 |
| Decoloured oak moss absolute 10 % sol. * | 3 |
| Natural degreased civet 10 % sol. * | 3 |
| Lily absolute 1 % sol. * | 2 |
| Orange blossom absolute 10 % sol. * | 2 |

-continued

| | |
|---|---|
| Jasmine absolute | 2 |
| Rose absolute | 1 |
| Musk ketone | 4 |
| Trichloromethylphenylcarbinyl acetate | 2 |
| Colourless Tolu resin absolute 10 % sol. | 1.5 |
| *in diethyl phthalate | |

By adding to 99.5 g. of this mixture 0.5 g. ** of 2,6,6-trimethyl-1-vinylacetyl-1-cyclohexene the composition obtained was more powerful than the basic composition and had an improved diffusion as well as a very natural richness.
** (as a 10 % solution in diethyl phthalate)

EXAMPLE 58

Perfume composition of the floral type

A floral type composition was prepared by mixing the following ingredients (parts by weight):

| | |
|---|---|
| Rhodinol | 24 |
| l-Citronellol | 21 |
| Chemically pure geraniol | 12 |
| Phenylethyl alcohol | 24 |
| Linalool | 2.5 |
| Farnesol | 2 |
| Eugenol | 0.5 |
| Methyleugenol | 2 |
| Neryl isobutyrate | 0.5 |
| Phenylethyl phenylacetate | 0.5 |
| Geranyl acetate | 1 |
| Guaiol acetate | 0.5 |
| Citral 10 % sol. * | 2.5 |
| Nonanol 10 % sol. * | 0.5 |
| Nonanal 10 % sol. * | 0.5 |
| Decanal 1 % sol. * | 2 |
| Undecanal 10 % sol. * | 0.5 |
| Deterpenated geranium oil | 1.5 |
| Phenylethylsalicylate | 0.5 |
| *in diethyl phthalate | |

By adding to 98.5 g. of this mixture 1.5 g. of 2,6,6-trimethyl-1-hydroxy-1-crotonoyl-2-cyclohexene the composition obtained was more powerful than the basic composition and had an improved diffusion as well as a very natural richness.

EXAMPLE 59

Preparation of a flavour composition for monastery type liquor

A flavouring composition for monastery type liquors was prepared by mixing together the following ingredients (parts by weight):

| | |
|---|---|
| Oil of Neroli | 5 |
| Oil of Clove | 20 |
| Oil of Cardamone | 25 |
| Oil of nutmeg | 25 |
| Oil of cinnamon | 25 |
| Lemon oil | 35 |
| Oil of sweet orange | 65 |
| Angelica seed oil | 75 |
| Peppermint oil | 75 |
| Oil of bitter orange | 200 |
| Angelica root oil | 445 |
| Total | 995 |

2,4,6,6-Tetramethyl-1-trans-crotonoyl-1-cyclohexene (5 g.) was added to 99.5 g. of the above mixture which was then called the test composition. A control composition resulted from the addition of 5 g. of Angelica root oil to 99.5 g. of the above mixture.

A liquor base was prepared by mixing the following ingredients:

| | |
|---|---|
| Alcohol 64 o.p. (96 %) | 325 ml. |
| wine alcohol (74 %) | 100 ml. |
| sugar syrup (65 %) | 10 ml. |
| water | 565 ml. |
| Total | 1000 ml. |

The liquor base was flavoured by adding to 100 kg. thereof 10 g. of the flavouring compositions. The finished liquor samples were tasted by a panel of tasters in the same manner as described in Example 46. All members of the panel declared with no hesitation that the test sample had a rounder taste than the control and at the same time a red berry character.

When in the above example, 2,4,6,6-tetramethyl-1-transcrotonoyl-1-cyclohexene was replaced by 2,4,6,6-tetramethyl-1-trans-crotonoyl-1,3-cyclohexadiene similar results were experienced. However, the test samples were also judged to have a more flowery and less fruity character than those containing 2,4,6,6-tetramethyl-1-trans-crotonoyl-1-cyclohexene.

We claim:

1. A composition of matter consisting essentially of a compound having the formula

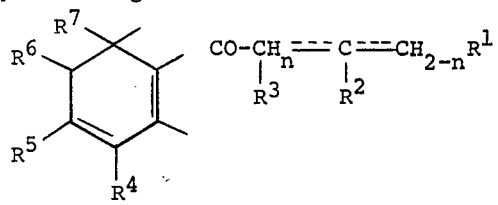

containing a double bond in the position 2' - or 3' - of the acyl side chain, the double bonds being represented by dotted lines, and wherein $n$ is zero or 1, $R^1$, $R^2$, and $R^3$ represent hydrogen or one of them a lower alkyl radical, and $R^4$, and $R^5$, $R^6$, and $R^7$ represent hydrogen or one of them a lower alkyl radical.

2. Compounds according to claim 1 wherein $R^5$, $R^6$ and $R^7$ represent hydrogen and $R^4$ a lower alkyl radical.

3. Compounds according to claim 2, wherein $R^4$ is methyl or ethyl.

4. Compounds according to claim 1 wherein $R^4$, $R^6$ and $R^7$ represent hydrogen and $R^5$ a lower alkyl radical.

5. Compounds according to claim 4, wherein $R^5$ is methyl or ethyl.

6. Compounds according to claim 1 wherein $R^4$, $R^5$ and $R^7$ represent hydrogen and $R^6$ a lower alkyl radical.

7. Compounds according to claim 6, wherein $R^6$ is methyl or ethyl.

8. Compounds according to claim 1 wherein $R^4$, $R^5$ and $R^6$ represent hydrogen and $R^7$ a lower alkyl radical.

9. Compounds according to claim 8, wherein $R^7$ is methyl or ethyl.

10. Compounds according to claim 1 wherein $R^4$, $R^5$, $R^6$ and $R^7$ represent hydrogen.

* * * * *

UNITED STATES PATENT AND TRADEMARK OFFICE
CERTIFICATE OF CORRECTION

PATENT NO. : 3,931,326

DATED : January 6, 1976

INVENTOR(S) : Ervin Kovats, et al.

It is certified that error appears in the above-identified patent and that said Letters Patent are hereby corrected as shown below:

Column 1, line 15 "$R^5$(first occurrence) should be --$R^6$--

Column 17, line 69 "aliphatic" should be --aliphatic or--

Column 20, line 21 "crotoncyl" should be --crotonoyl--

Column 23, third formula "$OH_2R^1$" should be --$CH_2R^1$--

Column 24, line 3 "agents" should be --agent--

Column 24, line 45 "$s_2O_3^=$" should be --$S_2O_3^=$--

Column 26, line 29 "vinylacetacetate" should be --vinylacetyl--

Column 33, line 57 "30-53° 10.001 Torr; should be --30-53°/0.001 Torr;--

Column 33, line 58 "53°65°-69°/0.001 Torr; should be --53-65-69°/0.001 Torr;--

Column 34, line 12 "extraation" should be --extraction--

Column 34, line 38 "Fraction I;" should be --Fraction I:--

Column 34, line 45 "ξppm;" should be --δppm;--

Column 35, line 55 "carefufl" should be --careful--

Column 35, line 58 "Fraction I;" should be --Fraction I:--

UNITED STATES PATENT AND TRADEMARK OFFICE
CERTIFICATE OF CORRECTION

PATENT NO. : 3,931,326
DATED : January 6, 1976
INVENTOR(S) : Ervin Kovats et al.

It is certified that error appears in the above-identified patent and that said Letters Patent are hereby corrected as shown below:

Column 37, line 1 "1-Bromo-3-methyl-butene" should be --
    a) 1-Bromo-3-methyl-butene--

Column 37, line 5 "ar" should be --at--

Column 37, line 11 "3,6-Dimethyl-5-hepten-2-one" should be --
    b) 3,6-Dimethyl-5-hepten-2-one--

Column 37, line 58 "$\nu$1620," should be --$\nu=1620$,--

Column 38, line 8 "Reaction" should be --Fraction--

Column 38, lines 18-19 "2,3,6,6-Tetramethyl-1-[1-hydroxy-2-butenyl]-2-cyclohexene" should be --
    e) 2,3,6,6-Tetramethyl-1-[1-hydroxy-2-butenyl]-2-cyclohexene--

Column 39, line 6 "bromides" should be --bromide--

Column 45, line 56 "pentencyl" should be --pentenoyl--

Column 46, line 39 "88°-90°10.1 Torr;" should be--
    88-90°/0.1 Torr;--

Column 49, line 20 "$n_D^{20}$ Dshould be --$n_D^{20}$--

Column 49, lines 69-70 "carryinng" should be --carrying--

Column 50, line 9 "$d_4^{20}$ 32 0.9390" should be --
    $d_4^{20}= 0.9390$--

United States Patent and Trademark Office
CERTIFICATE OF CORRECTION

PATENT NO. : 3,931,326             Page 3 of 3
DATED : January 6, 1976
INVENTOR(S) : Ervin Kovats et al.

It is certified that error appears in the above-identified patent and that said Letters Patent are hereby corrected as shown below:

Column 51, line 21 "$C_{13}Hh_{22}O$" should be --$C_{13}H_{22}O$--

Column 52, line 1 "Example 36 tCl" should be --Example 36--

Column 54, line 40 "1-Citronellol" should be --
and line 68   ℓ-Citronellol--

Column 55, line 33 "1-Citronellol" should be--
ℓ-Citronellol--

Column 57, line 18 "tested" should be --tasted--

Column 59, line 54 "1.4890;" should be --1.4890; $d_4^{20}=$ 0--

Column 62, line 21 "1-Citronellol" should be --
ℓ-Citronellol--

Column 62, lines 64 and 67 "99.5" should be --995--

Signed and Sealed this

Nineteenth Day of October 1976

[SEAL]

*Attest:*

RUTH C. MASON
*Attesting Officer*

C. MARSHALL DANN
*Commissioner of Patents and Trademarks*

UNITED STATES PATENT AND TRADEMARK OFFICE
CERTIFICATE OF CORRECTION

PATENT NO. : 3,931,326
DATED : January 6, 1976
INVENTOR(S) : Ervin Kovats et al.

It is certified that error appears in the above—identified patent and that said Letters Patent are hereby corrected as shown below:

Column 63, line 24, formula reads:

" 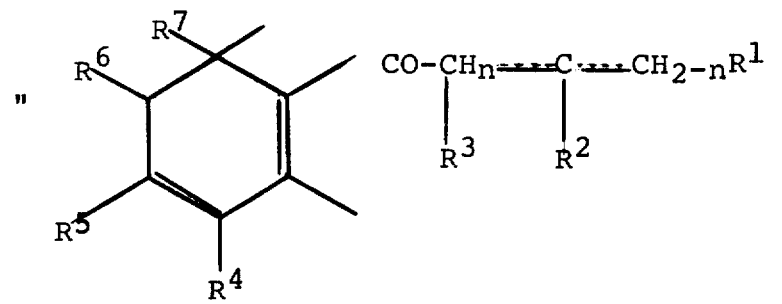 "

should read:

-- 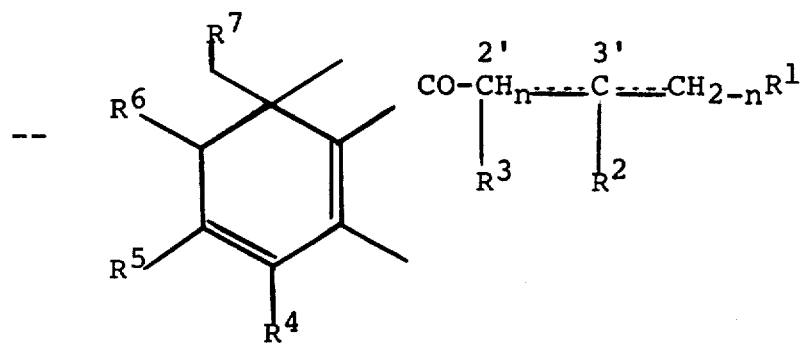 --

Signed and Sealed this

Eighteenth Day of January 1977

[SEAL]

Attest:

RUTH C. MASON
Attesting Officer

C. MARSHALL DANN
Commissioner of Patents and Trademarks